(12) United States Patent
Vandenbogart et al.

(10) Patent No.: US 8,753,324 B2
(45) Date of Patent: Jun. 17, 2014

(54) BODY ADHERING ABSORBENT ARTICLE

(75) Inventors: Thomas W. Vandenbogart, Slinger, WI (US); Adrienne R. Loyd, Neenah, WI (US); Garry R. Woltman, Appleton, WI (US); David J. Enz, Neenah, WI (US); Renee Sue Booms, Oshkosh, WI (US); Carmen Lira, Appleton, WI (US); Katie A. Boland, Menasha, WI (US); Ann Louise McCormack, Cumming, GA (US); Deborah S. Hannah, Appleton, WI (US); Mary McDaniel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 503 days.

(21) Appl. No.: 13/084,271

(22) Filed: Apr. 11, 2011

(65) Prior Publication Data

US 2012/0089107 A1 Apr. 12, 2012

Related U.S. Application Data

(63) Continuation of application No. 12/005,793, filed on Dec. 28, 2007, now Pat. No. 7,947,027.

(51) Int. Cl.
*A61F 13/15* (2006.01)
(52) U.S. Cl.
USPC ....... 604/385.17; 604/387; 604/400; 604/401
(58) Field of Classification Search
USPC ........ 604/385.17, 385.18, 386, 387, 400, 401
See application file for complete search history.

(56) References Cited

U.S. PATENT DOCUMENTS

| | | | |
|---|---|---|---|
| 2,842,897 A | 7/1958 | Finn | |
| 3,288,346 A | 11/1966 | Peppler | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,963,029 A | 6/1976 | Brooks | |
| 3,972,328 A | 8/1976 | Chen | |
| 4,072,151 A | 2/1978 | Levine | |

(Continued)

FOREIGN PATENT DOCUMENTS

DE 692 32 589 T2 12/2002
EP 0353972 A1 2/1990

(Continued)

OTHER PUBLICATIONS

American Society for Testing Materials (ASTM) Designation: D1300-53 T, "Tentative Specifications and Methods of Test for Laminated Thermosetting Decorative Sheets," pp. 148-166, issued 1953.

(Continued)

*Primary Examiner* — Melanie Hand
(74) *Attorney, Agent, or Firm* — Kimberly-Clark Worldwide, Inc.

(57) ABSTRACT

The present invention provides a body adhering absorbent article which is capable of absorbing bodily fluids. In this particular embodiment of the present invention, provided is an absorbent article which is specifically designed for attachment to a wearer's skin in the vulva region of the wearer's torso.

17 Claims, 9 Drawing Sheets

(56) References Cited

U.S. PATENT DOCUMENTS

| | | |
|---|---|---|
| 4,340,563 A | 7/1982 | Appel et al. |
| 4,488,928 A | 12/1984 | Ali Khan et al. |
| 4,505,976 A | 3/1985 | Doehnert et al. |
| 4,631,062 A | 12/1986 | Lassen et al. |
| 4,673,403 A | 6/1987 | Lassen et al. |
| 4,743,245 A | 5/1988 | Lassen et al. |
| 4,758,241 A | 7/1988 | Papajohn |
| 4,781,712 A | 11/1988 | Barabino et al. |
| 4,798,603 A | 1/1989 | Meyer et al. |
| 4,804,380 A | 2/1989 | Lassen et al. |
| 4,846,824 A | 7/1989 | Lassen et al. |
| 4,909,244 A | 3/1990 | Quarfoot et al. |
| 4,977,892 A | 12/1990 | Ewall |
| 5,051,259 A | 9/1991 | Olsen et al. |
| 5,114,419 A | 5/1992 | Daniel et al. |
| 5,147,938 A | 9/1992 | Kuller |
| 5,194,299 A | 3/1993 | Fry |
| 5,194,550 A | 3/1993 | Rance et al. |
| 5,221,275 A | 6/1993 | Van Iten |
| 5,277,954 A | 1/1994 | Carpenter et al. |
| 5,369,155 A | 11/1994 | Asmus |
| 5,382,400 A | 1/1995 | Pike et al. |
| 5,387,208 A | 2/1995 | Ashton et al. |
| 5,419,956 A | 5/1995 | Roe |
| 5,445,627 A | 8/1995 | Mizutani |
| H1602 H | 10/1996 | Brock |
| 5,611,790 A | 3/1997 | Osborn, III et al. |
| 5,618,281 A | 4/1997 | Betrabet |
| 5,618,282 A | 4/1997 | Schlangen |
| 5,632,736 A | 5/1997 | Block |
| 5,658,270 A | 8/1997 | Lichstein |
| 5,662,633 A | 9/1997 | Doak et al. |
| 5,669,894 A | 9/1997 | Goldman et al. |
| 5,706,950 A | 1/1998 | Houghton et al. |
| 5,714,225 A | 2/1998 | Hansen et al. |
| 5,759,560 A | 6/1998 | Dillon |
| 5,800,417 A | 9/1998 | Goerg Wood et al. |
| 5,807,367 A | 9/1998 | Dilnik |
| 5,811,116 A | 9/1998 | Gilman et al. |
| 5,830,202 A | 11/1998 | Bogdanski et al. |
| 5,885,265 A | 3/1999 | Osborn, III et al. |
| 5,897,546 A | 4/1999 | Kido et al. |
| 5,910,125 A | 6/1999 | Cummings et al. |
| 5,994,613 A | 11/1999 | Cummings et al. |
| 6,045,900 A | 4/2000 | Haffner et al. |
| 6,080,139 A | 6/2000 | Gallegos |
| 6,156,818 A | 12/2000 | Corzani |
| 6,177,482 B1 | 1/2001 | Cinelli |
| 6,187,989 B1 | 2/2001 | Corzani |
| 6,191,189 B1 | 2/2001 | Cinelli |
| 6,211,263 B1 | 4/2001 | Cinelli |
| 6,213,993 B1 | 4/2001 | Zacharias |
| 6,255,552 B1 | 7/2001 | Cummings et al. |
| 6,316,524 B1 | 11/2001 | Corzani |
| 6,336,935 B1 | 1/2002 | Davis et al. |
| 6,352,528 B1 | 3/2002 | Weber et al. |
| 6,362,389 B1 | 3/2002 | McDowall et al. |
| 6,365,645 B1 | 4/2002 | Cinelli |
| 6,369,126 B1 | 4/2002 | Cinelli |
| 6,386,203 B1 | 5/2002 | Hammerslag |
| 6,495,229 B1 | 12/2002 | Carte et al. |
| 6,566,575 B1 | 5/2003 | Stickels et al. |
| 6,582,411 B1 | 6/2003 | Carstens et al. |
| 6,616,643 B1 | 9/2003 | Costa |
| 6,617,490 B1 | 9/2003 | Chen et al. |
| 6,620,143 B1 | 9/2003 | Zacharias |
| 6,632,210 B1 | 10/2003 | Glasgow et al. |
| 6,641,569 B1 | 11/2003 | Coles |
| 6,657,009 B2 | 12/2003 | Zhou |
| 6,659,990 B1 | 12/2003 | Odorzynski et al. |
| 6,670,402 B1 | 12/2003 | Lee et al. |
| 6,702,796 B2 | 3/2004 | McFall et al. |
| 6,733,483 B2 | 5/2004 | Raufman et al. |
| 6,756,520 B1 | 6/2004 | Krzysik et al. |
| 6,803,420 B2 | 10/2004 | Cleary et al. |
| 6,997,915 B2 | 2/2006 | Gell et al. |
| 7,033,342 B2 | 4/2006 | Mizutani et al. |
| 7,045,559 B2 | 5/2006 | Yahiaoui et al. |
| 7,053,131 B2 | 5/2006 | Ko et al. |
| 7,122,022 B2 | 10/2006 | Drevik |
| 7,125,401 B2 | 10/2006 | Yoshimasa |
| 7,137,971 B2 | 11/2006 | Tanzer |
| 7,198,689 B2 | 4/2007 | Van Gompel et al. |
| 7,217,259 B2 | 5/2007 | McDaniel |
| 7,265,158 B2 | 9/2007 | Risen, Jr. et al. |
| 7,358,282 B2 | 4/2008 | Krueger et al. |
| 7,378,450 B2 | 5/2008 | Erkey et al. |
| 2001/0025163 A1 | 9/2001 | Brown et al. |
| 2001/0039407 A1 | 11/2001 | Widlund |
| 2002/0072725 A1 | 6/2002 | Kolby Falk |
| 2002/0193766 A1 | 12/2002 | Gell et al. |
| 2003/0004484 A1 | 1/2003 | Hammons et al. |
| 2003/0065302 A1 | 4/2003 | Kuroda et al. |
| 2003/0078554 A1 | 4/2003 | Drevik |
| 2003/0106825 A1 | 6/2003 | Molina et al. |
| 2003/0208112 A1 | 11/2003 | Schmidt et al. |
| 2004/0116883 A1 | 6/2004 | Krautkramer et al. |
| 2004/0122385 A1 | 6/2004 | Morman et al. |
| 2004/0151930 A1 | 8/2004 | Rouns et al. |
| 2004/0158221 A1 | 8/2004 | Mizutani et al. |
| 2004/0167488 A1 | 8/2004 | Bellucci et al. |
| 2004/0167491 A1 | 8/2004 | Mizutani |
| 2004/0209075 A1 | 10/2004 | Maloney |
| 2005/0010185 A1 | 1/2005 | Mizutani et al. |
| 2005/0014901 A1 | 1/2005 | Osae et al. |
| 2005/0059918 A1 | 3/2005 | Sigurjonsson et al. |
| 2005/0124948 A1 | 6/2005 | Morman et al. |
| 2005/0124960 A1 | 6/2005 | Ruman |
| 2005/0136023 A1 | 6/2005 | Yahiaoui et al. |
| 2005/0136077 A1 | 6/2005 | Yahiaoui et al. |
| 2005/0137549 A1 | 6/2005 | Lindsay et al. |
| 2005/0148984 A1 | 7/2005 | Lindsay et al. |
| 2005/0182378 A1 | 8/2005 | Bonelli et al. |
| 2005/0261652 A1 | 11/2005 | Digiacomantonio et al. |
| 2006/0058760 A1 | 3/2006 | Rosenfeld et al. |
| 2006/0058764 A1 | 3/2006 | Bohlen |
| 2006/0063322 A1 | 3/2006 | Hsu et al. |
| 2006/0079823 A1 | 4/2006 | Utterberg et al. |
| 2006/0089613 A1 | 4/2006 | Mizutani et al. |
| 2006/0129114 A1 | 6/2006 | Mason et al. |
| 2006/0142722 A1 | 6/2006 | Koenig et al. |
| 2006/0148917 A1 | 7/2006 | Radwanski et al. |
| 2006/0161125 A1 | 7/2006 | Bohlen et al. |
| 2006/0188940 A1 | 8/2006 | Cima et al. |
| 2006/0195053 A1 | 8/2006 | Oelund et al. |
| 2006/0206077 A1 | 9/2006 | Warren et al. |
| 2006/0224133 A1 | 10/2006 | Gannon et al. |
| 2006/0224134 A1 | 10/2006 | Luizzi et al. |
| 2006/0264884 A1 | 11/2006 | Carstens |
| 2007/0100313 A1 | 5/2007 | Luizzi |
| 2007/0124850 A1 | 6/2007 | Buettner |
| 2007/0250028 A1 | 10/2007 | Woltman et al. |
| 2007/0287973 A1 | 12/2007 | Cohen et al. |
| 2008/0021424 A1 | 1/2008 | Erdman |
| 2008/0057811 A1 | 3/2008 | Yahiaoui et al. |
| 2008/0147035 A1 | 6/2008 | Snell |
| 2008/0207779 A1 | 8/2008 | Yahiaoui et al. |
| 2008/0234647 A1 | 9/2008 | Arterburn |
| 2009/0036858 A1 | 2/2009 | Van Den Bogart et al. |
| 2009/0054864 A1 | 2/2009 | Lira et al. |
| 2009/0062762 A1 | 3/2009 | Himbergen et al. |
| 2009/0069771 A1 | 3/2009 | Yu et al. |
| 2009/0069780 A1 | 3/2009 | Plentovich et al. |
| 2009/0071862 A2 | 3/2009 | Snell |
| 2009/0171309 A1 | 7/2009 | Vandenbogart et al. |
| 2009/0182296 A1 | 7/2009 | Dennis et al. |
| 2009/0198203 A1 | 8/2009 | Lira et al. |
| 2009/0204090 A1 | 8/2009 | Dennis et al. |
| 2009/0204092 A1 | 8/2009 | Loyd et al. |
| 2010/0057034 A1 | 3/2010 | Dennis et al. |
| 2010/0121304 A1 | 5/2010 | Zhou et al. |
| 2010/0152693 A1 | 6/2010 | Lira et al. |
| 2010/0198177 A1 | 8/2010 | Yahiaoui et al. |
| 2011/0092945 A1 | 4/2011 | Carstens |

(56) References Cited

U.S. PATENT DOCUMENTS

FOREIGN PATENT DOCUMENTS

| | | |
|---|---|---|
| EP | 0 638 303 B1 | 11/1997 |
| EP | 0 850 628 A1 | 7/1998 |
| EP | 0 909 662 A2 | 4/1999 |
| EP | 0 609 236 B1 | 5/2002 |
| EP | 1407743 A1 | 4/2004 |
| GB | 2 284 767 A | 6/1995 |
| JP | 04-279159 A | 10/1992 |
| JP | 09-117473 A | 5/1997 |
| KR | 10-2001-0022000 A | 3/2001 |
| KR | 10-0563880 B1 | 3/2006 |
| WO | WO 93/07841 | 4/1993 |
| WO | WO 95/16424 | 6/1995 |
| WO | WO 98/27910 | 7/1998 |
| WO | WO 98/27912 | 7/1998 |
| WO | WO 98/27913 | 7/1998 |
| WO | WO 98/27915 | 7/1998 |
| WO | WO 98/27916 | 7/1998 |
| WO | WO 98/27917 | 7/1998 |
| WO | WO 98/27918 | 7/1998 |
| WO | WO 98/28015 | 7/1998 |
| WO | WO 98/28017 | 7/1998 |
| WO | WO 98/28019 | 7/1998 |
| WO | WO 98/28022 | 7/1998 |
| WO | WO 98/28023 | 7/1998 |
| WO | WO 98/47454 A1 | 10/1998 |
| WO | WO 98/55065 | 12/1998 |
| WO | WO 98/57609 A1 | 12/1998 |
| WO | WO 99/01094 | 1/1999 |
| WO | WO 99/01095 | 1/1999 |
| WO | WO 99/30659 | 6/1999 |
| WO | WO 00/00235 | 1/2000 |
| WO | WO 2006/028612 | 3/2006 |

OTHER PUBLICATIONS

"Antiperspirant Drug Products for Over-the-Counter Human Use: Final Monograph," Final Rule, Federal Register—Rules and Regulations, vol. 68, No. 110, Jun. 9, 2003, pp. 34273-34293.

Berner, G. et al. "Photoinitiators—An Overview", Journal of Radiation Curing, vol. 6, No. 2, Apr. 1979, pp. 2-9.

Lloyd, J. et al., "Female Genital Appearance: 'Normality' Unfolds," *BJOG: An International Journal of Obstetrics and Gynecology*, vol. 112, May 2005, pp. 643-646.

Mandavi, Alborz et al., "A Biodegradable and Biocompatible Gecko-Inspired Tissue Adhesive," PNAS, vol. 105, No. 7, Feb. 19, 2008, pp. 2307-2312.

Matsumoto, A., "Characteristic Polymerization Behaviour of Microgel-Like Poly(allyl methacrylate) Microspheres," Macromol. Symp., vol. 179, No. 1, 2002, pp. 141-152.

ized, causing discomfort to the wearer of the absorbent article. For example, the presence and absence of pressure from the absorbent article on the inner thighs as the user moves, which is often described by users as feeling "like a diaper", is one source which compromises comfort for users of conventional absorbent articles, including liners, ultra-thin absorbent pads and maxi pads. In addition, the movement of the user or deformation of the underwear while being worn may also cause the absorbent article to have a poor fit against the body of the user, which could result in leaks from the absorbent article.

BODY ADHERING ABSORBENT ARTICLE

This application is a continuation of application Ser. No. 12/005,793 entitled BODY ADHERING ABSORBENT ARTICLE and filed on Dec. 28, 2007 now U.S. Pat No. 7,947,027. The entirety of application Ser. No. 12/005,793 is hereby incorporated by reference.

FIELD OF THE INVENTION

The present invention relates generally to an absorbent article for absorbing bodily fluids.

BACKGROUND OF THE INVENTION

Absorbent personal care articles intended to absorb discharged bodily fluids are well known in the art. Such absorbent articles generally comprise a fibrous mass or other absorbent core which can absorb and hold body fluids. Similarly, it is well known that feminine care articles have been employed to absorb and hold liquids, such as urine and/or menses. A typical structure of an absorbent article includes a fluid impermeable back sheet, a fluid permeable top sheet and an absorbent core positioned between the back sheet and the top sheet. Prior absorbent articles have also included various other features to improve fluid handling, such as intake layers, distribution layers, retention layers and the like. In these absorbent personal care articles, the top sheet is the body-facing side of the absorbent article and the back sheet is the garment-facing side of the absorbent article.

Generally, the absorbent articles are held in place during use by using the wearer's waist and elastic materials in the waist portion of the absorbent product in place during use, in the case of pant-like garments, such as diapers and training pants, or by attaching the absorbent article to the underwear or undergarment of a user, in the case of pads or liners. Current methods of attaching the absorbent article to the underwear or undergarment of a user include placing an adhesive on the garment-facing side of the back sheet, having optional flaps (wings) that extend from the longitudinal sides of the absorbent article which wrap around the crotch portion of the underwear or undergarment of the user and a combination of the adhesive and the flaps.

It has also been suggested to use an adhesive to adhere the absorbent article to the skin of the user. However, the design of these absorbent articles was essentially the same as the absorbent articles which were attached to the underwear or undergarment of the user. That is, the adhesive is applied to the body-facing surface of the top sheet. Alternatively, in another design, a portion of the back sheet was wrapped around and over the top sheet. This portion of the back sheet which is wrapped around and over the top sheet becomes a body facing surface. An adhesive is applied to the portion of the back sheet which is wrapped over the top sheet. While these designs were effective for adhering the absorbent article to the skin of a user, these absorbent articles were not comfortable for users to wear, since the shape and size of the absorbent articles were the same as those absorbent articles which were attached to the undergarment or underwear of the user.

Similarly, absorbent articles that are attached to the underwear or undergarment of a user can also be uncomfortable for the user. This is because during normal movement of the body, portions of the body place opposed forces on the undergarment, which may cause the undergarment to be bunched or twisted. When this occurs, any absorbent article attached to the underwear or undergarment may also become bunched or Another disadvantage of conventional absorbent articles is that the silhouette or outline of the absorbent article may be visible to others through the clothing of the user. Even currently available ultra-thin absorbent articles may be visible through tight fitting outer clothing of a user. Therefore, conventional absorbent personal care articles do not always provide discretion for users.

There is a need in the art to provide users of absorbent articles with a discrete absorbent product, which is as easy to use as a conventional pad and is comfortable to wear and will effectively prevent or reduce premature leakage from the absorbent article.

SUMMARY OF THE INVENTION

Generally stated, the present invention provides a body-adhering absorbent article which is capable of absorbing bodily fluids.

In one embodiment of the present invention, provided is an absorbent article for attachment to a wearer's skin in the vulva region of the wearer's torso. The absorbent article has a shell having a first surface and a second surface, a first region where the first region has a pair of lateral side regions extending from the first region. This pair of lateral side regions each has a proximate end adjacent the first region and a distal end. The pair of lateral side regions and the first region define an opening in the shell. Attached to the second side of the shell is an absorbent structure, which is attached such that at least a portion of the absorbent structure is positioned in the opening in the shell. In addition, a majority of the opening of the shell has the absorbent structure positioned therein. The absorbent article of the present invention, when applied to a wearer, the first surface of the shell contacts to the wearer's skin surrounding vulva region of the wearer and the shell is sized and shaped such that the first surface of the shell only contacts the skin of the wearer proximate to the vulva region of the wearer.

In another embodiment of the present invention, the distal ends of each side region are adjacent to a second region, such that the second region joins each distal ends of the side regions together. This will provide for the opening being formed from the first region, the second region and the pair of lateral side regions. In an alternative embodiment, the distal ends of each side region are not connected to one another through the shell.

In another embodiment of the present invention, the first region forms an anterior portion and the second region forms a posterior portion of the absorbent article and the posterior portion is adapted to attach to the body of a user between the vulva region and the anal region of the body of the user. In addition, the anterior portion is adapted to attach to the mons Veneris region of a user. The absorbent article also may have a shell which has an anatomically correct shape for placement in the vulva region of a user. Generally the posterior portion of the shell has a protrusion extending upward from the first side of the shell.

In further embodiments of the present invention, the shell may be prepared from a wide variety of materials, such as a woven web, a foam, nonwoven web, a gel, a film, a sheet of a polymeric material or a laminate of one or more of these materials. Generally, the shell is prepared from a breathable material so that the user will be provided with comfort during use.

In another embodiment of the present invention, at least a portion of the first surface of the shell has adhesive properties. These adhesive properties provide a means to attach the absorbent article to the wearer's skin surrounding vulva region of the wearer's body. The first side of the shell may have an adhesive applied thereto. In a further embodiment of the present invention, the first side of the shell is essentially entirely covered by the adhesive.

In a further embodiment of the present invention, the absorbent structure has an absorbent core and a liquid impermeable backsheet. The absorbent core is positioned between the opening and the liquid impermeable backsheet or the second side of the shell and the liquid impermeable backsheet. Further the absorbent structure may further have a liquid permeable topsheet. When the topsheet is present, the absorbent core is positioned between the liquid permeable topsheet and the liquid impermeable backsheet.

In another embodiment of the present invention, the shell is sized and shaped such that the extent of the first area of the shell only contacts the skin proximate to the vulva of the wearer, and may attach to the pubic and/or the perineal regions of the body of the user.

The absorbent articles of the present invention may be used as a pantiliner, a sanitary napkin or an incontinence absorbent product. In addition, the absorbent article may be worn as an underwear substitute since the absorbent article does not need underwear to hold the absorbent article in place. As an underwear substitute, the absorbent article provides protection to the vulva area by creating a barrier between the clothing and the vulva.

In yet a further embodiment of the present invention, provided is a absorbent system having a shell with a first surface and a second surface, a first region having a pair of lateral side regions extending from the first region. The pair of lateral side regions each has a proximate end adjacent the first region and a distal end, and the pair of lateral side regions and the first region define an opening in the shell. The system further has a plurality of absorbent structures, each absorbent structure being adapted to be attached to the second side of the shell such that at least a portion of the absorbent structure is positioned in the opening in the shell. Generally, a majority of the opening of the shell has the absorbent structure positioned therein. When applied to the wearer, the first surface of the shell contacts to the wearer's skin surrounding vulva region and the shell is sized and shaped such that the first surface of the shell only contacts the skin of the wearer proximate to the vulva region of the wearer.

In a further embodiment of the system, the plurality of absorbent structures are made of at least one absorbent structure with a first absorbent capacity and at least one absorbent structure with a second absorbent capacity with the first absorbent capacity being different from the second absorbent capacity. In addition, there may be a plurality of shell materials, each having different attachment properties, shapes or sizes. The plurality of shell materials may provided in separate packages and the plurality of absorbent structures having different absorbent capacities are provided in different packages.

By providing the disposable absorbent article of the present invention, drawbacks of the conventional absorbent personal care articles are minimized.

DEFINITIONS

Figure 1:
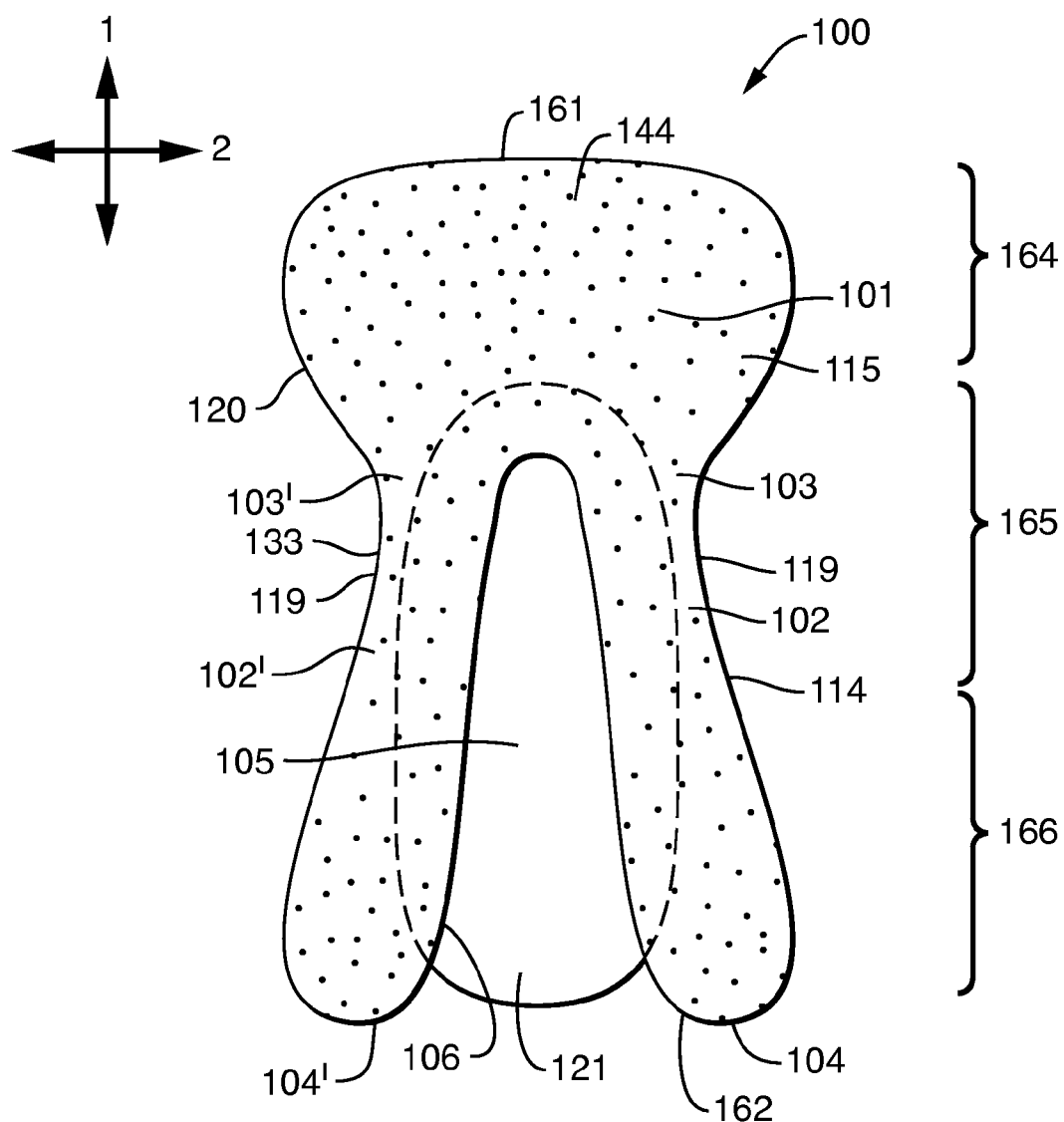
FIG. 1 shows a top view of an embodiment of an absorbent article of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, the term "polymer" generally includes, but is not limited to, homopolymers, copolymers, such as, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "body-facing surface" means that surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the term "absorbent structure" is intended to mean a configuration of an absorbent material which allows bodily fluids to be absorbed by the absorbent material.

DETAILED DESCRIPTION OF THE INVENTION

The absorbent product of the present invention provides an absorbent article which is designed to adhere to the body of a user in the area of the body of the user which may need bodily fluids absorbed. In one particular use of the absorbent article, the absorbent article is attached to the body of a female user to or around the vulva region of the body. By "to or around the vulva region", it is meant adjacent regions of the body of a female including the pubic region and the perinea region. When applied to or around the vulva region of the female body, the absorbent article may be used as a pantiliner, sanitary napkin or incontinence article. In addition, the absorbent article may be worn as an underwear substitute since the absorbent article of the present invention does not need underwear hold the absorbent article in place. As an underwear substitute, the absorbent article provides protection to the vulva area by creating a barrier between the outer clothing and the vulva of a user. When worn as an underwear substitute, the absorbent article serves to protect the outer clothing of the wearer from bodily discharges from the vulva region of the user's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region.

Figure 2:
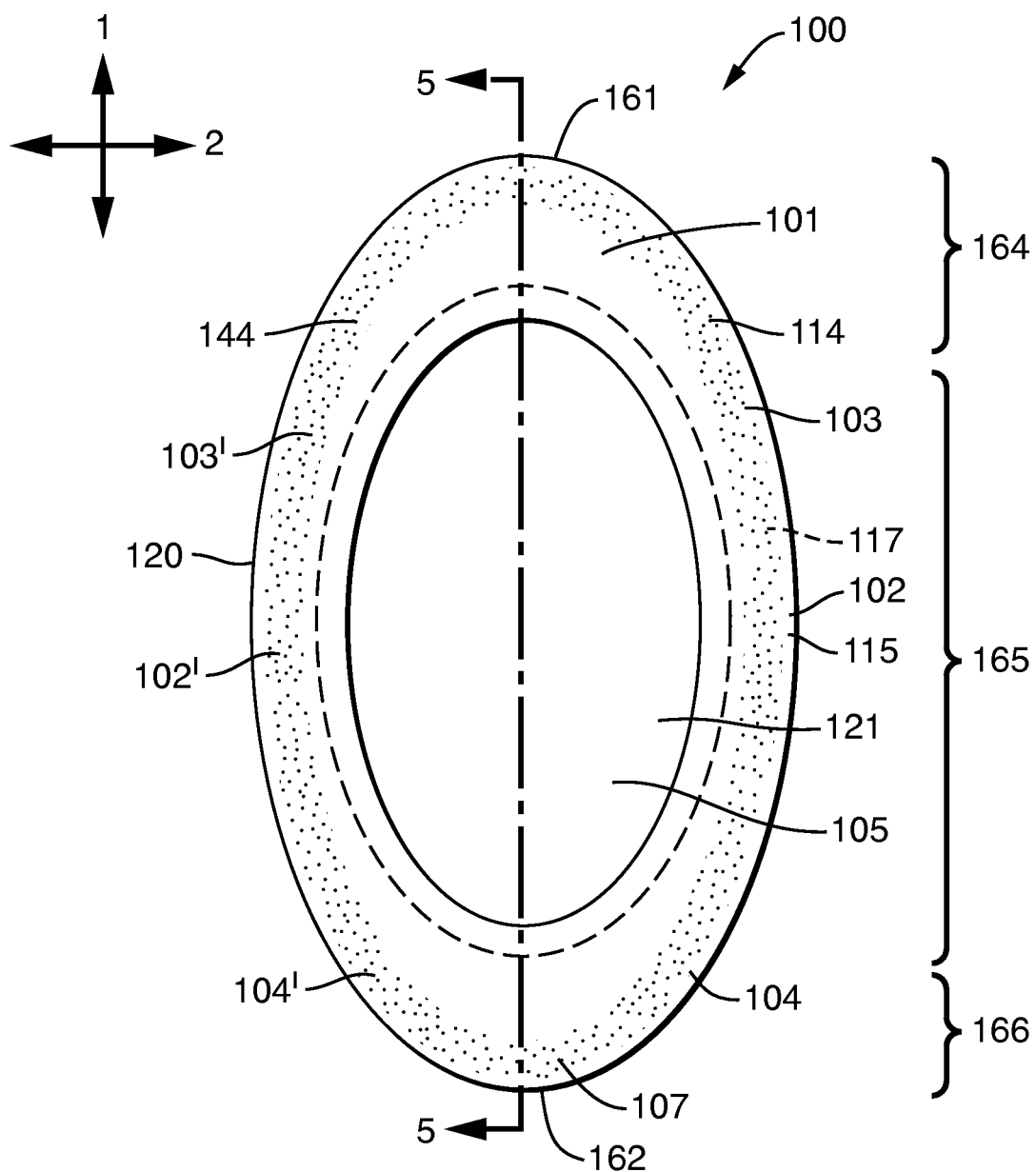
FIG. 2 shows a top view of an embodiment of an absorbent article of the present invention
Figure 3:
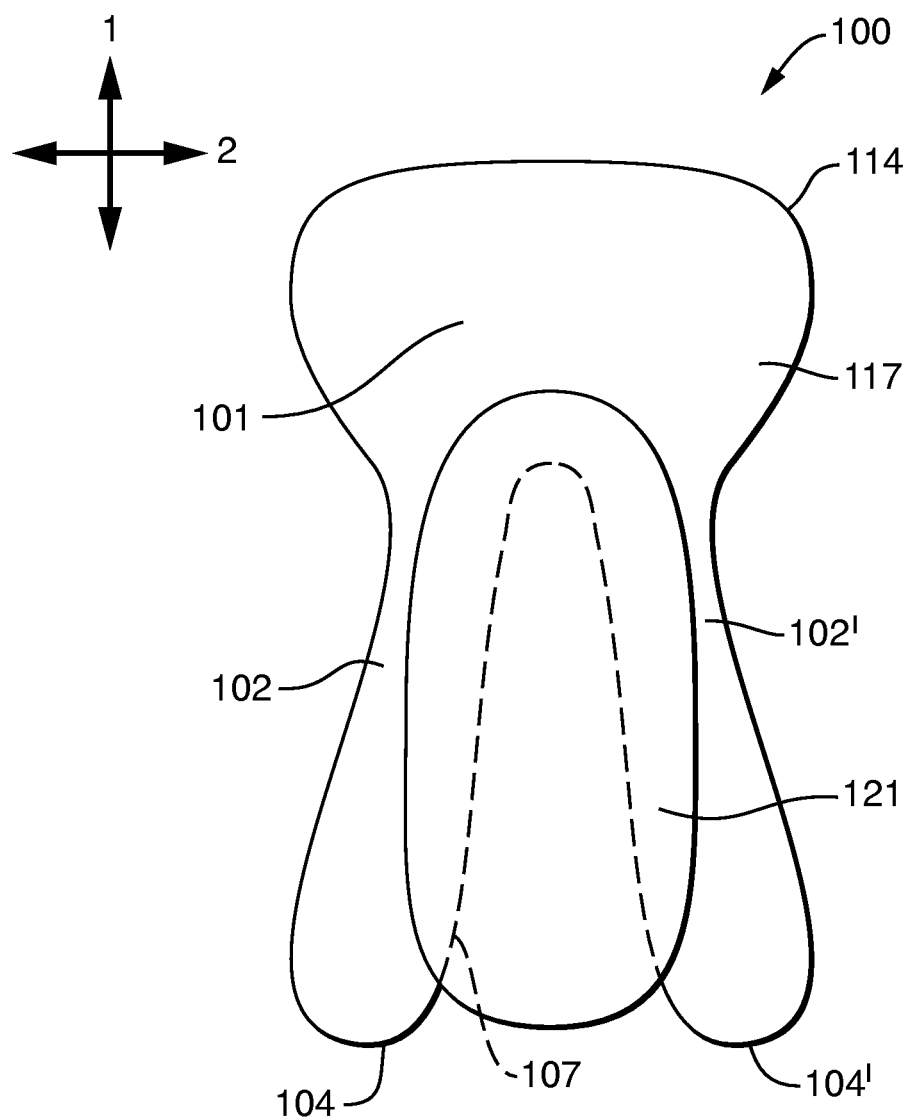
FIG. 3 shows a bottom view of the absorbent article shown in the embodiment of absorbent article of the present invention shown in FIG. 1.
Figure 4:
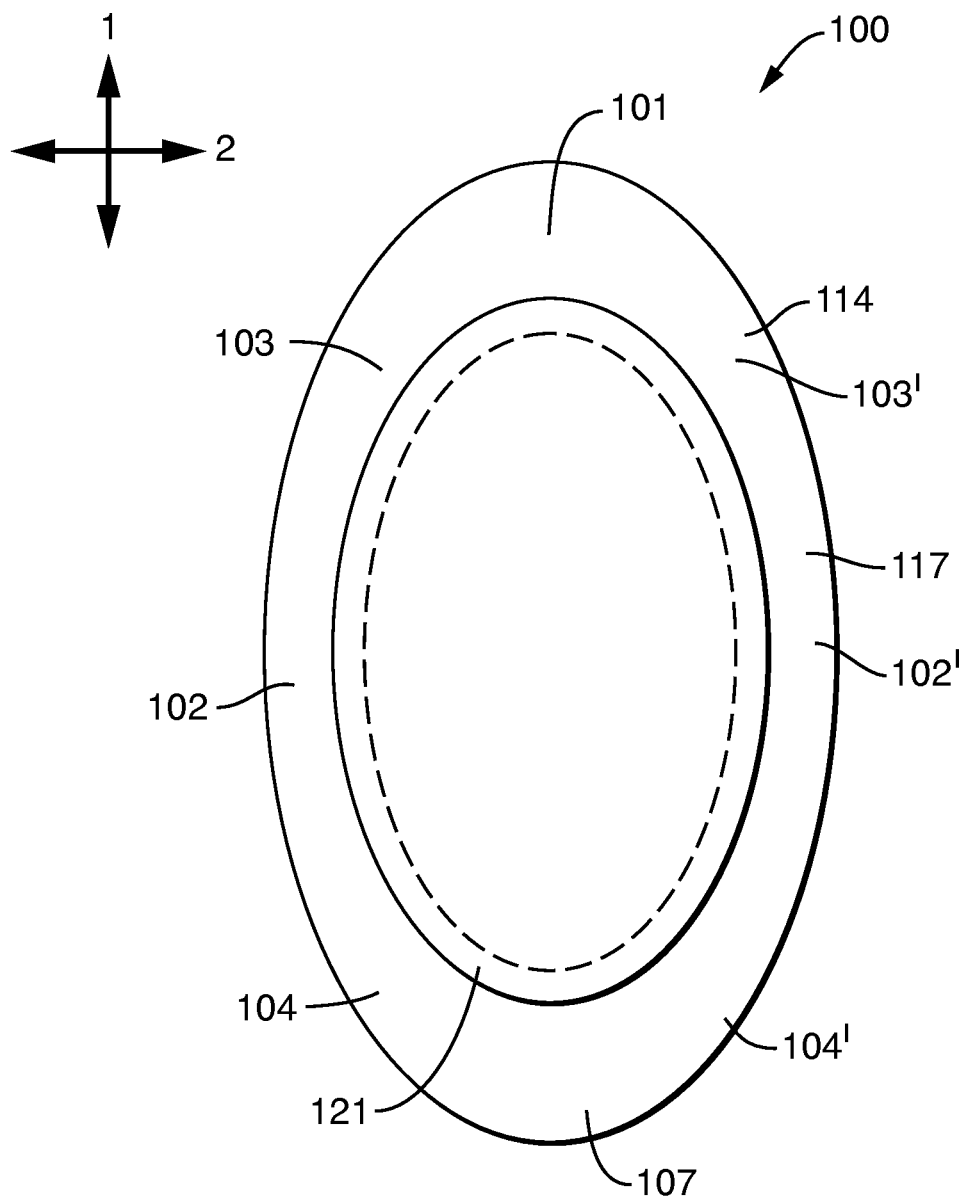
FIG. 4 shows a bottom view of the absorbent article shown in the embodiment of absorbent article of the present invention shown in FIG. 2.

To gain a better understanding of the present invention, attention is directed to the Figures of the present specification. As is shown in each of the Figures, in particular FIGS. 1 and 2, the absorbent article 100 has a longitudinal direction 1 and a lateral direction 2. One component of the absorbent article 100 is a shell 114. This shell 114 has a first side 115, as shown in FIGS. 1 and 2 and a second side 117, as is shown in FIGS. 3 and 4. The shell 114 serves to provide the overall contour or silhouette of the absorbent article of the present invention. In addition, the shell 114 also provides a surface for attachment or adhesion of the absorbent article 100 to the body of a user.

The first side 115 of the shell 114 is the body facing side of the absorbent article 100 and the second side 117 of the shell 114 is the garment facing side of the absorbent article. The shell 114 of the absorbent article 100 has a first region 101. This first region 101 has a pair of lateral side regions 102, 102' extending from the first region. This pair of lateral side regions each has a proximate end 103, 103' adjacent the first region 101 and a distal end 104, 104'. The pair of lateral side regions 102, 102' and the first region 101 together define an opening 105 in the shell 114. This opening 105 may be open near the distal ends 104, 104' of the lateral side regions 102, 102', as shown in FIG. 1 or, as shown in FIG. 2, the lateral side regions 102, 102' may be joined at the distal end 104, 104' to form a second region 107. The portions of the lateral side regions 102, 102' and the first region 101 adjacent the opening 105 form a circumference or edge 106 around the opening 105. This circumference or edge 106 typically has thickness in the z-direction 3 which is about equal to the thickness of the shell. However, the thickness of the edge may be increase or decreased to improve comfort for a user or performance of the absorbent article.

The absorbent article 100 further has an absorbent structure 121 attached to the second side 117 of the shell 114, as is shown in FIGS. 1-6. At least a portion of the absorbent structure 121 is positioned in the absorbent article such that a majority of the opening 105 in the shell has the absorbent structure 121 positioned therein, as can be seen in FIGS. 1 and 2. In one particular embodiment, the entire area of the opening 105 has the absorbent structure 121 positioned therein. Generally to hold the absorbent structure in place, a portion of the absorbent structure 121 is attached to the second side 117 of the shell 115. Suitable methods of attaching the absorbent structure 121 to the second side 117 of the shell 115 includes adhesives, mechanically bonding the absorbent structure 121 to second side 117 using bonding means such as ultrasonic bonding, heat and pressure bonding and the like, which are discussed in more detail below.

In one embodiment of the present invention, the opening 105 in the shell may be a hole, which is devoid of any material, or and in another embodiment of the present invention the opening 105 may be a region which is permeable to body fluids. If the opening is a region which is permeable, the opening may have a material such as hydrogel or similar material that will allow body fluids to flow through the material.

In one embodiment, the first side 115 of the shell 114 is adapted to be the body contacting side of the absorbent article. The first region 101, the lateral sides 102, 102' and the second region 107, when present, on the first side 115 of the shell 114 are designed or adapted to contact, attach or adhere to the wearer's skin. In one particular embodiment, the first region 101 of the shell 114 is designed or adapted to contact a female wearer's skin surrounding the vulva region of the female torso when the absorbent article 100 is applied to the wearer. By "designed or adapted to contact a female wearer's skin surrounding the vulva region of the female torso", it is meant that the size and shape of the shell 114, including the first region and the lateral side regions and second region, if present, is such that the shell 114 fits in the vulva region and possibly the surrounding pubic region and perinea regions of the female torso. Generally, the shell 114 is sized and shaped such that the extent of the first side 115 of the shell 114 only contacts and attaches or adheres to the skin surrounding and proximate to the vulva area and possibly the pubic and perinea regions of the wearer. In addition to contacting the skin in the vulva, pubic and perinea regions of the wearer, the first side 115 of the shell 114 may also contact and attach or adhere to any hair in the vulva area of the user which may be present. The first side 115 of the shell 114 is what holds the absorbent article in place on the body of a user.

To gain a better understanding of the vulva region and surround regions of the female body, a general description of the anatomical structures can be found in *The Illustrated Running Press Edition of the American Classic Gray's Anatomy* (1974) by Henry Gray and *Structure and Function in Man* (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include gluteal region and perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle and the sides by lines extending through the greater trochanters. The shape of the gluteal region is roughly hemi-spherical and convex, and is determined by a series of muscles including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction; the mons pubis, labia majora and minora, clitoris, meatus urinarius and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides the thigh line.

The vulva region includes the female external genitalia and generally includes the anterior and central regions of the perineum. The mons pubis [or veneris] is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region general has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et. al., *BJOG: An International Journal of Obstetrics and Gynecology*, May 2005, Vol. 112, pp. 643-646 and is included herein by reference.

As a woman ages, many changes occur to the vulva region. Skin begins to lose its elasticity and hangs more loosely from the body. In addition, the fat pads tend to be reduced, changing the topography of the vulva region. As a result, there is a need for a product which can be adapted to these changing conditions.

When the absorbent article of the present invention is positioned for use on a user, generally the first side 115 of the shell, including the first region 101, the lateral side regions 102, 102' and the second region 107, if present, are positioned on the user outside the labia majora of the user. This will allow any fluid coming from the vulvo-vaginal area of the body of a user to pass through the opening 105 present in the shell 114, so that the fluid may flow into the absorbent structure 121. The opening 105 could be an area which is devoid of the shell material or any other material. Alternatively, the opening may be a permeable area, which is permeable to body fluids, containing a material which is permeable. Typically, the absorbent structure 121 is the portion of the absorbent article which provides absorbency to the absorbent article. In an alternative embodiment, the first side 115 of the shell 114 may also provide some absorbency to the absorbent article. For example, the second first side 115 of the shell 114 may contain an absorbent material integrated into the shell 114, such that the first side of the shell 114 has some degree of absorbency. The first side 115 of the shell 114 may have an absorbent material coated or impregnated into the shell material.

When the second region 107 is present, as shown in FIG. 2, the entire opening 105 is surrounded by the shell 114. When the second region 107 is not present, as shown in FIG. 1, the opening 105 has an unbound end, meaning that the distal ends 104, 104' of the lateral side regions 102, 102' are not connected. Each configuration of the absorbent articles shown in FIGS. 1 and 2 have advantages. For example, the configuration shown in FIG. 1, where the second region 107 is not present in the absorbent article 100, the absorbent article 100 may provide more comfort to the user when being worn. That is, in use of the absorbent article 100, the first region 101 is designed to be placed towards the anterior portion of the vulva region of the user. By not having the second region, the absorbent article 100 will not be positioned in the perinea region of the user, which may provide improved comfort to the user. Alternatively, by having the second region 107 present, the absorbent article may provide superior leak protection to the user, by creating a seal completely surrounding the labia majora of a user. As a result, any and all fluid leaving the vaginal cavity will be confined to the absorbent article.

Figure 6:
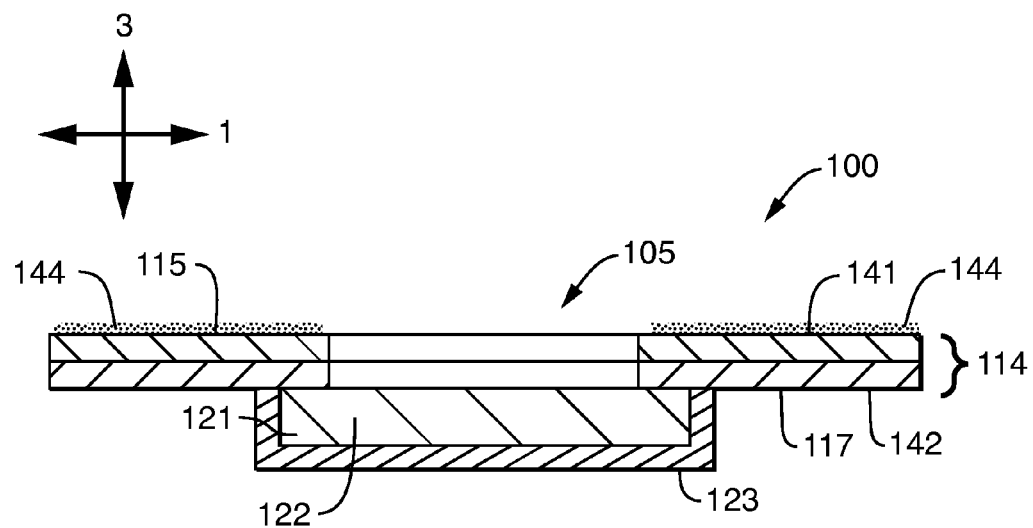
FIG. 6 shows a side cut-away view of an embodiment of an absorbent article of the present invention shown in FIG. 2 along line 5-5 having a two-layer shell.

The shell 114 of the absorbent article 100 may be prepared from a variety of materials. The shell may include a layer constructed of any material which will function to be operatively liquid impermeable. The shell 114 may, for example, include a polymeric film, a woven fabric, a nonwoven fabric or the like, as well as combinations or composites thereof. For example, the shell 114 may include a polymer film laminated to a woven or nonwoven fabric. A laminate shell 14 structure is shown in FIG. 6, having an upper layer 141 and a lower layer 142, wherein the upper layer 141 is the body-facing side of the shell 114 and the lower layer 142 is the garment facing side of the shell 114. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 114 can operatively permit a sufficient passage of air and moisture vapor out of the absorbent article 100, particularly out of an absorbent structure 121 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials which are extensible may be used in the present invention, including, for example foams. One example of a suitable foam is a polyurethane foam with a negative Poissons ratio. Examples of extensible backsheet materials are described in U.S. Pat. No. 5,611,790, issued Mar. 18, 1997, to Osborn, I I I et al., herein incorporated by reference in its entirety. Other materials that are inherently breathable, such as polyurethanes, may be used to form the shell 114.

In one particular embodiment of the present invention, the shell 114 may be a laminate of a woven or nonwoven fabric with a silicone polymer, wherein the silicone polymer has adhesive properties. The second side 117 of the shell will be woven or nonwoven fabric and the first side 115 of the shell will be silicone polymer. One commercially available laminate is an Oleeva Fabric® I available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 115 of the shell material. Relating this particular structure to the Figures, in FIG. 6, the silicone polymer is the upper layer 141 of the shell 114 and the nonwoven or woven layer is the lower layer 142 of the shell.

Bicomponent films or other multi-component films can also be used as the shell 114 material. In addition, woven and/or nonwoven fabrics which have been treated to render them operatively liquid-impermeable can also be used as an effective shell 114 material. Another suitable shell material can include foams. Examples of foam include a closed-cell polyolefin foam, a foam with a negative Poissons ration and other similar foams. Other suitable polymeric materials include, a polyurethane polymer material, a silicone polymer or other similar materials. Silicone polymers having naturally occurring adhesive properties, or silicone polymers having a silicone adhesive layer applied thereto are of particular interest for the shell material. Such silicone polymers will allow the first side 115 of the shell 114 to adhere to the body of the user without the need of an additional adhesive. These materials may be laminated to another material, such that the second side 117 of the shell 114, which is the garment facing side of the absorbent article 100 is laminated to the other material, so that the adhesive nature of the silicone polymer does not adhere the garment of under garments of the user. In another embodiment of the present invention, the shell material may be prepared from an interpenetrating polymer network or two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move with the skin of the user during normal use and normal movements by the user during use. By "normal movement by the user" it is meant any movement that normally occurs during use of the absorbent article, including walking, running, sitting, standing, kneeling, riding a bicycle, exercising, playing sports, getting into and out of an automobile, and other similar movements made by users when wearing an absorbent article. The shell should not be too rigid, such that the shell detaches from the skin of the user during use and the shell should not be so flexible that the shell tends to twist and bunch during use. The shell should have sufficient flexibility to conform to the skin of the user and become similar to a second skin of the user. The shell should also have the ability to remain attached to the body of the user under moist or wet conditions.

Generally, the shell material should have sufficient thickness to allow the shell 114 to mold to the body of the user, but not too thick that the shell 114 becomes uncomfortable for the user to wear. In addition, the shell 114 should not be so thin that it ineffectively forms a seal with the skin of the user when applied to the user, or becomes detached from the skin of the user during use and normal movement of the user during use or that it does not adequately conform to the shape and skin of the user at the point of attachment to the user. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material and the ability of the material to assume the shape of the skin of the user at the location of use, which is typically the vulva region of a user.

The second side 117 of the shell 114 may form a portion of the garment-facing side of the absorbent article 100 when worn by a user. The shell material should be selected such that the second side 117 of the shell will freely move against the undergarment or clothing of a user. One way to achieve this result is to have the second side 117 of the shell 114 to have a fairly low coefficient of friction. This will allow the second side 117 of the shell 114 to freely move against the undergarment or other clothing worn by the user. If the second side 117 of the shell 114, does not freely move against the undergarment or other clothing worn by the user, the absorbent article may catch on the undergarment or clothing, which may result in the absorbent article being prematurely and undesirably removed from the user or may cause the absorbent article to be shifted from its desired placement against the body of a user.

In order to achieve the desired coefficient of friction on the second side 117 of the shell 114, the materials used to prepare the shell could be selected such that the second side 117 of the shell material will inherently have the desired coefficient of friction. Alternatively, the second side 117 of the shell 114 may be treated with a coating composition, such a polytetrafluoroethylene containing coating, a silicone containing coating or other similar coating having low coefficient of friction properties. Alternatively, the shell 114 could be made from a laminate of two or more materials such that the first side 115 of the shell 114 is prepared from a material which meets the needed properties of the first side 115, while the material selected for the second side 117 of the shell 114 meets the desired coefficient of friction such that the second side 117 will free move against the undergarment or garment being worn by a user.

Figure 5:
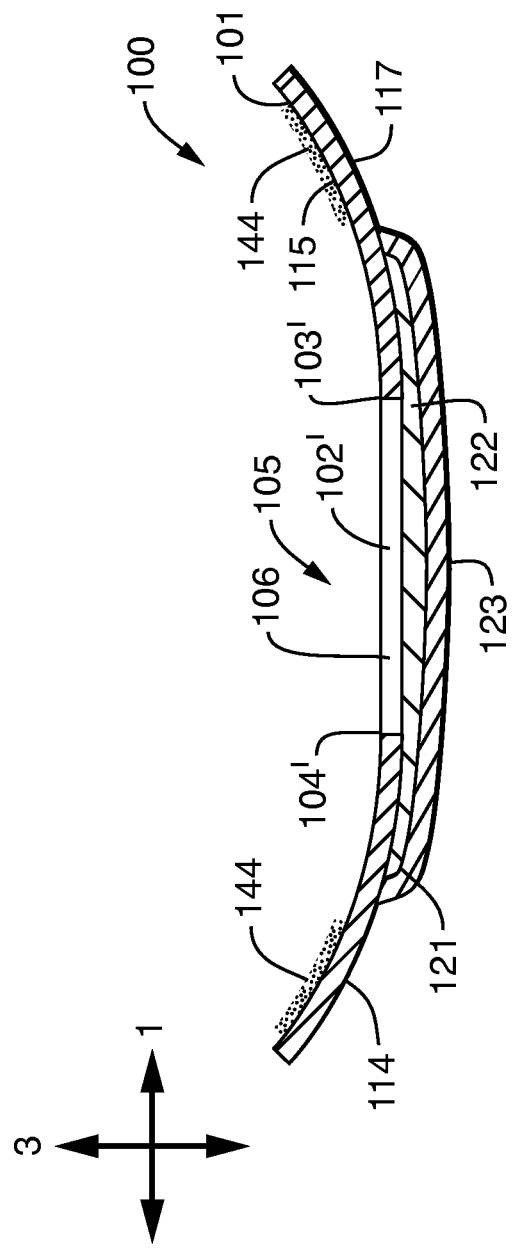
FIG. 5 shows a side cut-away view of an embodiment of an absorbent article of the present invention shown in FIG. 2 along line 5-5.

The shell 114 of the absorbent article 100 may be flat or may have a three-dimensional shape. As is shown in FIG. 5, which is a cross-sectional side view of the absorbent article the shell 114 has a three-dimensional concave shape. Alternatively, as is shown in cross-sectional side views of FIG. 6, the shell 114 may have a generally flat shape. By providing the absorbent article 10 with a three-dimensional concave shape, as is shown in FIG. 5, placement of the article may be easier for the user. Generally, the three-dimensional shape could be such that it closely matches the overall general curvature of the vulva region and optionally the pubic and perinea regions of most women, when the absorbent article is used as a pantiliner, sanitary napkin or a feminine incontinence article. To form the shell 114 with a three-dimensional shape, the shell may be molded in any manner known to those skilled in the art, for example heat molding. The manner in which the three-dimensional shape is imparted to the shell 114 is not critical to the present invention.

When the shell 114 is a generally flat shape, for example as shown in FIG. 6, meaning that the shell does not have a third dimension other than thickness, the shell 114 should be made to be flexible enough that the shell 114 can conform to the body of the user at the point of attachment. In addition to being flat, the overall shape of the shell 114 may be contoured, as is shown in FIG. 1. In one embodiment, the contour shape may be such that the narrowest point of the contour is in the crotch area of the shell 114 nearest the vulva region, as is shown in FIG. 1. The contour shape shown in FIG. 1 is one of many possible shapes, in which the shell 114 and absorbent article may be prepared. Other shapes may be used, without departing from the scope of the present invention. Generally, the shape selected should be such that the shell 14 and absorbent article 100 are comfortable for the user to wear, while providing leakage protection to the user. It is noted that a contour shape may also be used in conjunction with a three-dimensional shell. Further discussion of the overall shape of the absorbent article may be found below.

The shell may be any desired color or may be translucent. In addition, the shell may have a matte finish, satin finish or a smooth finish. The particular finish color or translucency can be a matter of choice for the manufacturer of the absorbent article of the present invention. However, providing a shell which is translucent may assist the user in placing the absorbent article 100 prior to use, since the user may be able to see where the article is placed compared to the genitalia of the user.

The absorbent structure 121 is designed to absorb body exudates, including menstrual fluid, blood, urine, and other bodily fluids, such as sweat and vaginal discharges. The absorbent structure 121 has a longitudinal direction 1 and a lateral direction 2 and is shown in FIGS. 1-4, and a thickness in the z-direction 3, as is shown in FIGS. 5 and 6. This absorbent structure 121 may be a single layer or may be multiple layers. Typically, the absorbent structure 121 has an absorbent core 122 and a generally liquid impermeable backsheet 123. This absorbent core 122 may contain one or more layers of absorbent materials. That is, the absorbent core 122 may be a single layer of absorbent materials or may be a multilayer structure. Each of the layers of the absorbent core 122 can contain similar materials or different materials. In the absorbent article 100 of the present invention, the materials which may be used to form the absorbent core 122 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 122 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 122 may have other properties including extensibility, which will allow the absorbent core to be extended or fit to a particular user. One example of extensible absorbent cores is described in U.S. Pat. No. 5,611,790, issued Mar. 18, 1997, to Osborn, III et al., herein incorporated by reference in its entirety.

In one embodiment, the absorbent core 122 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxy functional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Selection of the actual materials used for the absorbent core 122 is within the skill of those skilled in the art. The actual materials used for the absorbent core are not critical to the present invention.

The generally liquid impermeable backing sheet 123 is present in the absorbent structure 121 to prevent fluid entering the absorbent core 122 from flowing through the absorbent core 122 and onto a garment or undergarment being worn by a user. Suitable liquid impermeable backing sheets include, for example, a polymeric film, a woven fabric, a nonwoven fabric or the like, as well as combinations or composites thereof. Generally, any material that may be used as the shell material describe above may be used as the backing sheet 123 of the absorbent structure 121. The liquid impermeable backing sheet 123 may be a polymeric film, a woven fabric, a nonwoven fabric or the like, as well as combinations or composites thereof. For example, the liquid impermeable backing sheet 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid impermeable backing sheet 123 can operatively permit a sufficient passage of air and moisture vapor out of the absorbent article 100, particularly out of an absorbent structure 121 while blocking the passage of bodily fluids and odors often associated with bodily fluids. An example of a suitable materials for the liquid impermeable backing sheet 123 can include a breathable, microporous film, such as those described in, for example, U.S. Pat. No. 6,045,900 to Haffner et al., the entire disclosure of which is incorporated herein by reference and made a part hereof.

The side of the backing sheet 123 which faces the undergarment or garments of a user should have a low coefficient of friction for the same reasons that the second side 117 of the shell should have a low coefficient of friction. This will allow the garment facing side of the backing sheet 123 to move freely against the undergarment or clothing of a user. If the garment facing side of the backing sheet 123 does not freely move against the undergarment or other clothing worn by the user, the absorbent article may catch on the undergarment or clothing, which may result in the absorbent article or the absorbent structure being prematurely and undesirably removed from the user or may cause the absorbent article to be shifted from its desired placement against the body of a user. In addition by having both the garment facing side of the backsheet 123 and the second side 117 of the shell freely move against the undergarment or clothing of the user, the body attached absorbent article will be comfortable for a user to wear and may provide improved protection since the undergarment or clothing will not cause the absorbent article to shift during use.

Generally, the absorbent structure will be positioned adjacent to the second side 117 of the shell 114, as can be clearly seen in FIGS. 1-6. By "adjacent to the shell", it is meant that the that the absorbent structure 121 is directly in contact with the second side 117 of the shell 114 or may be separated by one or two additional layers or a construction or pressure sensitive adhesive. The absorbent structure should be positioned such that the absorbent core 122 is beneath the opening 105 so that any fluid flowing through the opening 105 will come into contact with the absorbent core 122.

In addition to the absorbent core 122, the absorbent structure 121 may have other additional layers which aid the absorbent core 122 in capturing and holding the bodily fluid into the absorbent core 122. These other layers, when present, in combination with the absorbent core 122 form the absorbent structure 121 of the absorbent article 100. There may be a single layer or multiple layers in addition to the absorbent core 122 in the absorbent structure 121.

One particular example of an additional layer which may be used in addition to the absorbent core 122 in the absorbent structure 121 is a top sheet 124, which is generally a liquid permeable material, which allows bodily fluids to pass through the top-sheet into the absorbent core. The top sheet 124 also may provide a user with a dry feeling by separating the absorbent core 122 from the body of the user. That is, the top sheet 124 is placed between the absorbent core 122 and the body of the user and such that the absorbent core 122 is between the top sheet 124 and the shell 114.

Optionally, the top sheet 124 may be formed from one or more materials. The top sheet 124 should be able to manage different body excretions depending on the type of product. In feminine care products, often the top sheet 124 must be able to handle menses and urine. In addition, the top sheet 124 may be comfortable, soft and friendly to the user's skin. In the present invention, the top sheet 124 may include a layer constructed of any operative material, and may be a composite material. For example, the top sheet can include a woven fabric, a nonwoven fabric, a polymer film, a film-nonwoven fabric laminate or the like, as well as combinations thereof. Examples of a nonwoven fabric usable in the top sheet 124 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet 124 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet is a film or a film laminate, the film should be apertured or otherwise be made to allow fluids to flow through the top sheet to the absorbent core.

Other examples of suitable materials for the top sheet 124 are composite materials of a polymer and a nonwoven fabric material. The composite materials are typically in the form of integral sheets generally formed by the extrusion of a polymer onto a nonwoven web, such as a spunbond material. In a particular arrangement, the top sheet layer 124 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 122). The selected arrangement of liquid permeability is desirably present at least on an operative portion of the top sheet 124 that is appointed for placement on the body-side of the article. The top sheet 124 can provide comfort and conformability, and can function to direct bodily exudates away from the body and toward the absorbent core 122. The top sheet 124 can be configured to retain little or no liquid in its structure, and can be configured to provide a relatively comfortable and non-irritating surface next to the body tissues of a wearer. In the present invention, the top sheet 124 positioned over the absorbent core may have a surface which is embossed, printed or otherwise imparted with a pattern.

Additional layers or substrates, including for example, the liquid acquisition and distribution layer, also referred to as a surge or transfer layer, and an optional tissue layer are also incorporated into the absorbent structure 121 of the absorbent product 100, for example, between the top sheet 124 and the absorbent core 122. The distribution layer may be shorter than the absorbent core or have the same length as the absorbent core 122. The distribution layer serves to temporarily hold an insulting fluid to allow the absorbent core sufficient time to absorb the fluid, especially when a superabsorbent material is present.

In another embodiment, the absorbent core, transfer layer and other components, such as tissue layers, may be free floating (unattached) between the shell 114 and the top sheet 124, and only are secured along only the peripheral edges thereof. Alternatively, the absorbent core 122, transfer layer, if present, and any other layer or component, if present, may be attached to one or both of the second side 117 of the shell 114 and top sheet 124 and/or to each other.

The absorbent structure 121, including the absorbent core 122, is generally attached to the second side 117 of the shell 114, such that the absorbent core is positioned under the opening 105 in the shell. The absorbent structure 121 may be attached to the shell 114 in a permanent manner, meaning that the absorbent structure is generally intended not to be removable by the user of the absorbent article 100. Alternatively, the absorbent structure 121 may be made to be removably attached to the shell, such that the absorbent structure 121 may be removed by a user of the absorbent article 100 and replaced with the same absorbent structure 121 or with another new absorbent structure 121. When the absorbent structure 121 is attached to the shell 114 in a permanent manner, meaning that the absorbent structure is not intended to be removed by the user, a construction adhesive may be used. Examples of usable construction adhesives include any adhesive which will effectively hold the absorbent structure 121 in place, so as not to be separated from the shell 114.

Commercially available construction adhesives usable in the present invention include, for example Rextac adhesives available from Huntsman Polymers of Houston, Tex., as well as adhesives available from Bostik Findley, Inc, of Wauwatosa, Wis. Other means may be used to hold the absorbent structure 121 to the shell, including heat bonding, ultrasonic bonding or other similar mechanical attachments.

When the absorbent structure 121 is removably attached, the absorbent structure 121 is held in place to the second side 117 of the shell 114 by a means which will allow the user to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 121 in place on the second side 117 of the shell 114 include pressure sensitive adhesives available from National Starch and, having offices in Bridgewater, N.J. 08807. By providing an absorbent structure 121 which is removable, the shell 114 may be reused several times without the need to again place the shell 114 when the absorbent structure needs to be replaced. Other means, such as mechanical attachment may also be used to removably attach the absorbent structure 121 to the shell 114. Also by having a removable absorbent structure 121, the absorbent structure can be selected by the user prior to use. This would allow the user to select an appropriate level of protection for a given day or allow the user to select a size or shape of the absorbent which the user finds to be more comfortable. When the absorbent structure 121 is removable, and adhesively attached to the shell 114, the adhesive could be designed to remain on the shell or remain only on the absorbent structure. Generally, the adhesive should be placed on the absorbent structure 121, since this will provide fresh adhesive to hold the new absorbent in place each time the absorbent structure 121 is replaced. If the adhesive is present on the absorbent structure 121, a release sheet may be place over the adhesive so that the adhesive is not contaminated with dirt or debris which may have an adverse effect in holding the absorbent structure 121 to the shell 114.

To aid a user in replacing the absorbent structure 121, placement aid may be present on the shell 114 and/or the absorbent structure. Suitable placement aids include the use of color, tactile indicators or any other means that would assist the user in replacing a removed absorbent structure.

Figure 7:
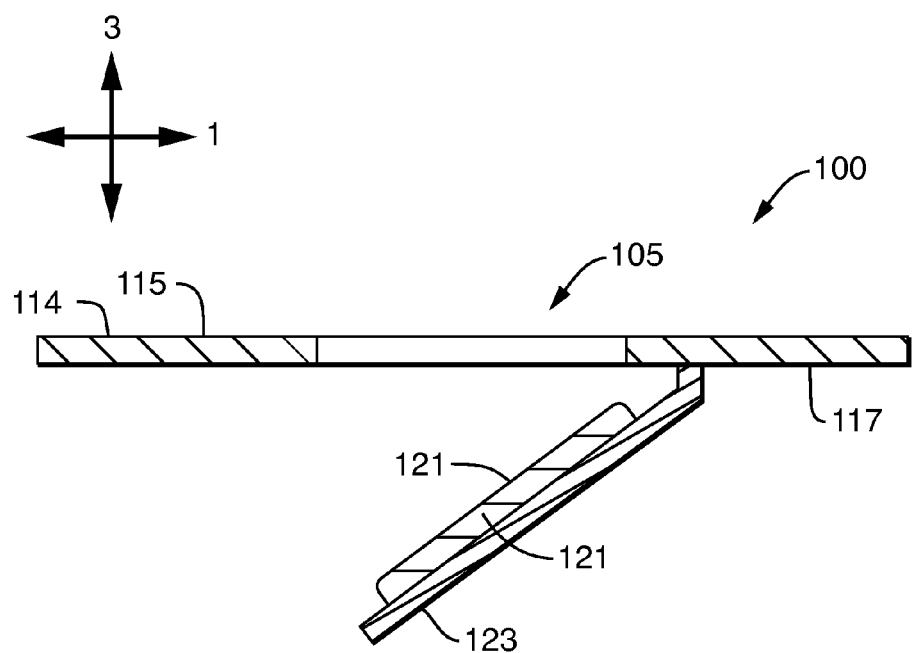
FIG. 7 shows a cross-sectional view of an embodiment of an absorbent article of the present invention having a hinged absorbent structure.

Another important advantage of having an absorbent structure which is removable is that the user may be able to perform normal bodily functions, such as urination. By having the absorbent which is removable, a user could remove the absorbent, urinate and replace the absorbent. This would alleviate the need of a user to have to replace the entire absorbent article 100 in order to form bodily functions. As another alternative, the absorbent structure 121 could be attached to the shell in such a manner that the absorbent structure is hinged with a hinging means, as is shown if FIG. 7.

The absorbent structure 121 may a relatively flat structure, as shown in FIG. 6 or the absorbent structure 121 curved to match the shape of the shell 114, as is shown in FIG. 5. The size, location and shape of the absorbent structure 121 may also be selected for an intended use. For example, in an overnight use, the absorbent may be located further back on the user towards the perinea region of the user. In an overnight use, the absorbent structure may be larger than in a product intended for daytime use. In a daytime use, the absorbent structure will generally be centrally located in the vulva region.

In an alternative embodiment of the present invention, the shell 114 material may also be provided with some absorbency in addition to the absorbent structure 121. One way to achieve absorbency in the shell is to have the shell 114 prepared from a material which is a laminate of two or more materials. The first side 115 of the shell 114 contains an absorbent material within the body facing side of the laminate. For example, superabsorbent particles or materials may be incorporated into the material making up the body facing layer of the laminate. Another way is to place a very light coating onto the first side 115 of the shell material, wherein the coating contains a superabsorbent particles or materials. Of course other absorbent materials, other than superabsorbent materials may be used in place of or in addition to the superabsorbent materials.

The absorbent core 122 of the absorbent structure 121 may be located entirely within the opening 105 in the shell 114, or the absorbent core 122 of the absorbent structure may extend past the opening 105 in the shell, as is shown in FIGS. 5 and 6, meaning that a portion of the absorbent core 122 contacts or is facing the second side 117 of the shell 114. Alternatively, the absorbent structure 121 may extend past the ends 104, 104' of the shell 114 or the second region 107 of the shell.

The liquid impermeable layer 123 may be a polymeric film, a woven fabric, a nonwoven fabric or the like, as well as combinations or composites thereof. For example, the liquid impermeable layer 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid impermeable layer 123 can operatively permit a sufficient passage of air and moisture vapor out of the absorbent article 100, particularly out of an absorbent structure 121 while blocking the passage of bodily fluids and odors often associated with bodily fluids. An example of a suitable materials for the liquid impermeable layer 123 can include a breathable, microporous film, such as those described in, for example, U.S. Pat. No. 6,045,900 to Haffner et al., the entire disclosure of which is incorporated herein by reference and made a part hereof. Other materials that may be used in preparing the impermeable layer 123 include materials which are inherently breathable, such as polyurethanes.

As is stated above, the first side 115 of the shell 114 either directly or indirectly attaches to the body of a user. Stated another way, the shell is the body attachment member and the first area 115 is the portion of the shell 114 which is attached to the body of the user. Depending on the material selected for the shell, the shell may actively attach to the body of the user using electrostatic means; suction means or a body adhesive may be placed on the first side 115 of the shell 114 to attach the absorbent article to the body of a user. Electrostatic means which can be used is by selecting the shell material to be a material which has an affinity for the body of a user, such that the shell material "clings" to the body of the user. Examples of such materials include ethylene vinyl acetate, low density polyethylene and other similar materials know to those skilled in the art. Suction means may be achieved by shaping the shell to conform to the body of the user, much like a contact lens fits to the eye. Generally, suction means can be achieved by forming the shell 114 into a three-dimensional shape. The easiest way to achieve body attachment is to place a body adhesive in the first side 115 of the shell 114.

A body adhesive 144 is positioned on the first side 115 of the shell 114. The body adhesive 144 contacts the skin and hair, if present, in the vulva region and possibly the public region and/or the perinea region of the wearer's body, thereby supporting and holding the absorbent article 100 against the body of the wearer during use. The body adhesive 144 can overlie a portion of the first side 115 or can overlie the first side 115 of the shell 114. Generally, the body adhesive 144 will be present on at least the outer portion first side of the shell near the edge 120 of the absorbent article 100. The adhesive may cover the entire first side 115 of the absorbent article (not shown in the drawings). Alternatively, the body adhesive 144 may be placed on a portion of the first side, as is shown in FIGS. 1 and 2. The body adhesive 144 may also be placed in a pattern of the first side 115 of the absorbent article. The body adhesive 144 can be applied to the first side 115 of the shell 114 of using any known process including inkjet printing, screen printing or extruding the body adhesive 144 from one or more nozzles, slot coating and the like.

Generally, any pressure sensitive adhesive known to those skilled in the art may be used, provided that the pressure sensitive adhesive is not a known irritant to human skin or that the adhesive is so aggressive that it causes pain to the user when the absorbent article is removed from the skin. It is also desirable that the adhesive is selected such that the adhesive does not leave a substantial amount of an adhesive residue on the surface of the skin of the user, when the absorbent article 10 is removed by the user after use. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Additional examples of pressure sensitive adhesives include hydrogels, hydrocolloids, acrylics based adhesives, and rubber based adhesives, such as Kraton based adhesives.

The body adhesive 144 may be positioned on the first side 115 of the shell 114 in an open pattern or a closed pattern. By "open pattern" is meant that the adhesive can have an intermittent or discontinuous pattern which does not substantially encircle the entire opening 105. For example, there may be breaks in the body adhesive at certain portions of the first side 115. "Closed pattern" means the adhesive 144 would encircle the entire opening 105 in the shell. In one embodiment, the pattern of the body adhesive 144 will substantially surround the cover the first side 105 and substantially surround the opening 105. An example of an "open" pattern of the adhesive would be to have individual beads of adhesive applied in a discontinuous fashion. In the present invention, the closed pattern can be advantageous since the body adhesive 144 may form a seal with the body of the user which will assist in preventing leaks from the absorbent article 100. The body adhesive may form a dam, which may prevent leaks from the entire perimeter of the absorbent article 100.

In one embodiment of the present invention, the body adhesive 144 may be placed on the entire first side 115 of the shell 114, as is shown in FIG. 1. In another alternative embodiment of the present invention, as is shown in FIG. 2, the body adhesive 144 may placed along the outer portions of the first side 115 near the periphery of the shell 114, such that no adhesive is near the opening 105. The body adhesive 144 may also be placed on the absorbent structure 121 positioned on the second side 117 of the shell 114 to help hold the absorbent article in place on the user. Generally, however, the body adhesive 144 is confined to being placed on the first side 115 of the shell 114, since placing the body adhesive on an area of the absorbent product 100 which contacts the female genitalia such as the labia majora may cause discomfort to the wearer of the absorbent product 100.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 144 to the body-contacting first side 115 of the absorbent article 100. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 $g/m^2$, and generally less than about 400 $g/m^2$. Generally, the weight of the adhesive is at least 20 $g/m^2$. Typically, the adhesive is applied in an amount of about 100 to about 400 $g/m^2$. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the user.

Generally, the body adhesive 144 is applied in a manner which is symmetrical about the longitudinal axis 1 which bisects the absorbent article 10 and divides the absorbent article 100 into substantially equal portions. This symmetrical pattern provides the wearer a balanced feel when wearing the absorbent article 100. The symmetrical pattern also reduces the perception of any associated discomfort when the absorbent article 100 is removed from the body.

Figure 8A:
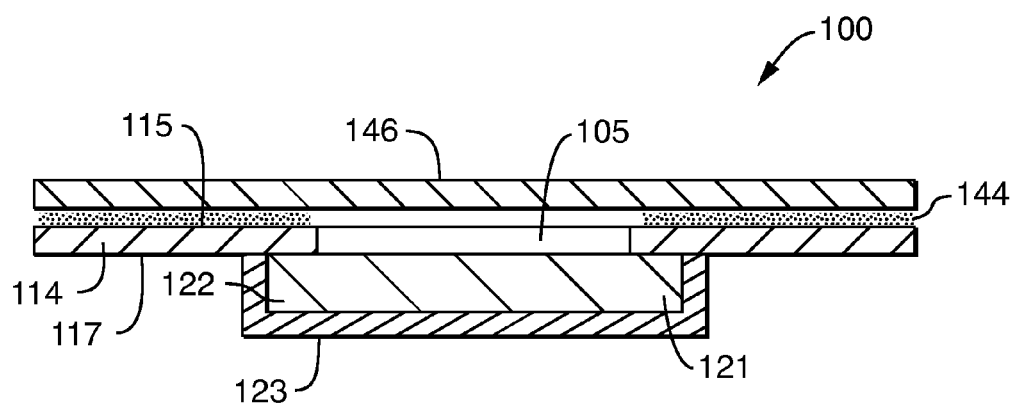
FIGS. 8A and 8B each show an absorbent article of the present invention having a release sheet applied thereto.
Figure 8B:
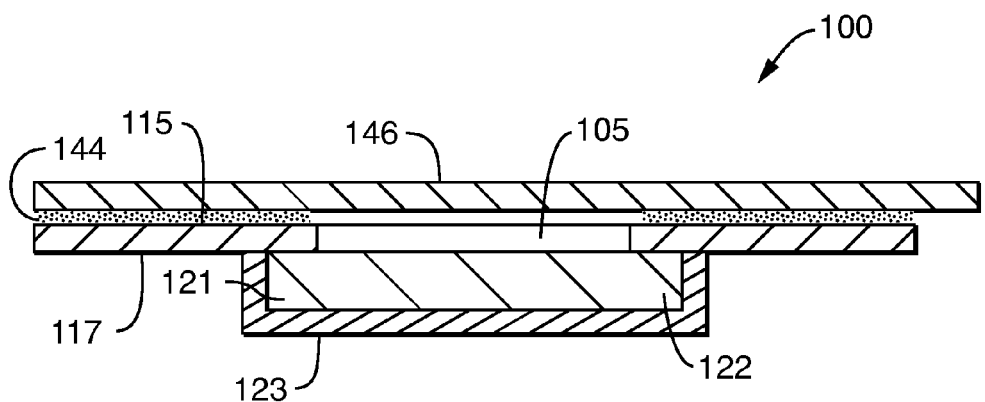

As is shown in FIGS. 8A and 8B, to protect the body adhesive 144, a peel sheet or release sheet 146 may be used to prevent the body adhesive 144 from becoming contaminated, thus loosing its ability to stick to the body of an user and/or prematurely adhering to an unintended surface. Suitable materials for use as a peel strip 146 are well known in the art and are commercially available. Examples of suitable peel sheets or release sheets include, a silicone coated Kraft paper, a silicone coated film or the like. Other release coating includes coating containing polytetrafluoroethylene. The peel sheet or release sheet 146 may extend beyond one or both of the ends and/or sides of the shell, as shown in FIG. 8B. Alternatively, the release sheet 46 may be sized to only cover the body adhesive on the first side 115 of the shell 114, as is shown in FIG. 8A. In yet another embodiment of the present invention, the release sheet may extend beyond the adhesive at one or more locations, such as one of the ends or one of the sides of the shell as is shown in FIG. 8C by providing the release sheet 146 with a tab 147 for the user to grasp to remove the release sheet 146 from the absorbent article 100 and the body adhesive 144 on the absorbent article 100. When the release sheet 146 extends beyond the adhesive, it is generally easier for the user to remove the release sheet 146 to place the absorbent article 100 for use.

Alternatively, the release sheet 146 may be provided with a pressure sensitive adhesive to hold the release sheet 146 in place when the absorbent article is devoid of an adhesive for body attachment. In this configuration, the release sheet 146 serves to protect the absorbent structure and first side of the shell from dirt and damage prior to use.

In another alternative, a release sheet may not be necessary. For example, the absorbent article may be rolled, folded onto itself or stacked upon each other. In these configurations, a release sheet is not needed. If rolled, the body adhesive 144 will generally contact the second side 117 of the shell 14 or the liquid impermeable backing sheet 123 of the absorbent structure. The body adhesive 144 should releasably stick to one second side of the shell by readily releasing when unrolled by the user or wearer. In addition, the body adhesive 144 should not leave a residue on the second side 117 of the shell 114, of the backing sheet 123. This should similarly occur when the absorbent articles 100 are stacked upon each other such that the body adhesive 144 of one article will attach the second side 117 of the shell and/or backing sheet of a second article. In another possible configuration, the absorbent article 100 may be folded along the longitudinal axis 1 of the lateral axis such that the body adhesive 144 in one area comes into contact with body adhesive in another area. In the folded configuration, the body adhesive should be selected such that the body adhesive will release from itself when manipulated by a user.

The dimensions and shape of the shell 114 should be such that it is appropriately sized for its intended use. The same is true for the size and shape of the absorbent structure 121 and the size of the opening 105. Generally, the size and shape of the absorbent structure 21 will dictate the size of the shell 114. The shape of the shell 114 is selected so that the absorbent article will have a comfortable feeling for the user, thereby providing protection against leaks and preventing the absorbent article from becoming dislodged from the body of the user during use. Generally, the shell 114 will be curved to fit the body of a user. The shell 114 also generally gives the absorbent article 100 its overall size and shape in the longitudinal 1 and lateral 2 directions. That is, the shell is generally longer and wider than the absorbent structure, as can be seen in the figures. In other words, the shell 114 will be wider in the lateral direction 2 than the absorbent structure 121, and the shell will be longer in the longitudinal direction 1 than the absorbent structure 121. As is mentioned above, it is possible for the absorbent structure 121 to be longer than the shell 114 but it is not generally wider.

When the absorbent article 100 is intended for use as a pantiliner, a sanitary napkin or a feminine incontinence article, the shell 114 should be wider and longer than the absorbent structure 121 attached to the second side 117 of the shell 114. The opening 105 in the shell 114 should generally be at least as wide and as long as the labia majora of the user. This will prevent the shell 114 from contacting the sensitive parts of a user's body. The absorbent structure 121 should be as large as or larger than the opening 105. As a result, to fit most women, the absorbent structure 121 is longer in the longitudinal direction 1 than it is wide in the lateral direction 2 of the absorbent structure. Generally, for most women, the labia majora are generally between about 40 mm and about 70 mm in width and between about 80 mm and 150 mm in length. Ideally, the absorbent structure 121 and opening 105 should be wider than the labia majora and slightly longer that the labia minora and slightly longer than or equal to the labia majora. Generally, the absorbent structure 121 and opening 105 should be between about 40 mm and 90 mm in width in the lateral direction 2 and between about 95 mm and about 150 mm in length in the longitudinal direction 1. The shape of the absorbent structure 121 and opening 105 will generally tend to be oblong and may be an oval, a rectangle, tear drop shaped, hourglass shaped or racetrack shaped. As can be seen in FIGS. 1 and 2, the absorbent structure 121 may be generally elliptical or oval in shape to match the size and shape of the vaginal area of most women.

Generally, the shape of the shell 114 may vary from a generally oval shape, as shown in FIGS. 2 and 4, to a shape which is a generally hourglass-like shape, shown in FIGS. 1 and 3. By a generally hourglass shape, it is meant shape in which the sides 119 of the shell 114 converge towards one another at a point along the longitudinal axis 1 of the shell 114 to form a narrowest portion 133 of the absorbent article 100. Generally, the hourglass-like shape provides a cut-out for the user's legs. By having an hourglass-like shape, the shell 114 will not be attached to the legs of a user during use. This will provide more comfort for the user of the absorbent article 100. The shape of the shell 114 should be selected such that the absorbent article 100 will be comfortable to wear, while providing very effective leakage protection to the user. The shell 114 and the absorbent structure 121 should be able to adapt to the curvature of a users body during use. Other possible shapes for the shell 114 not specifically shown may also be used, provided that the shape will provide comfort to the user of the absorbent article.

To obtain an effective attachment of the absorbent article to the user, when the absorbent article is used as a sanitary napkin or an incontinence article, generally the width of the of the shell should be at least 10 mm on either side of the labia majora. Generally, the shell 114 of the absorbent article 100 will have a width, in the lateral direction 2, between about 50 mm up to 200 mm or more. Typically, the shell will be between about 60 and 120 mm at its narrowest point. This will allow the shell 114 to have a first side 115 that can be effectively attached to the skin of a user on either side of the labia majora.

In addition, the absorbent article 100 may also be configured to have an anterior portion 164, a central portion 165 and a posterior portion 166, as is shown in FIG. 1. As used herein, the term "anterior" refers to the direction towards the front of the wearer during use. As used herein, the term "posterior" refers to the direction towards the back of the wearer during use. A particular embodiment is shown in FIG. 1 of an absorbent article having a configuration designed to fit specific areas of the vulva region of a user. By providing specific portions for attachment to specific areas of the body of the user, the absorbent article may be configured to better fit the body of the user. The anterior portion 164 of the absorbent article will be the portion of the absorbent article between the absorbent structure 121 and the first end 161 of the absorbent article 100. The posterior portion 166 of the absorbent article 100 will be the portion of the absorbent article between the absorbent structure 121 and the second end 162 of the absorbent article 100. Generally, the posterior portion 166 will be designed to be placed between the vagina area and the anal area of the user. The anterior portion 164 is designed to be placed on the mons Veneris region of a female user. The central portion 165 of the absorbent article 10 is designed to cover the vagina area of the user and the skin area surrounding the lateral sides of the labia majora, when the absorbent article is used as a pantiliner, sanitary napkin or an incontinence article. In an alternative use, the absorbent article of the present invention may also be used as an underwear replacement, or a guard for a swimming suit.

Figure 9A:
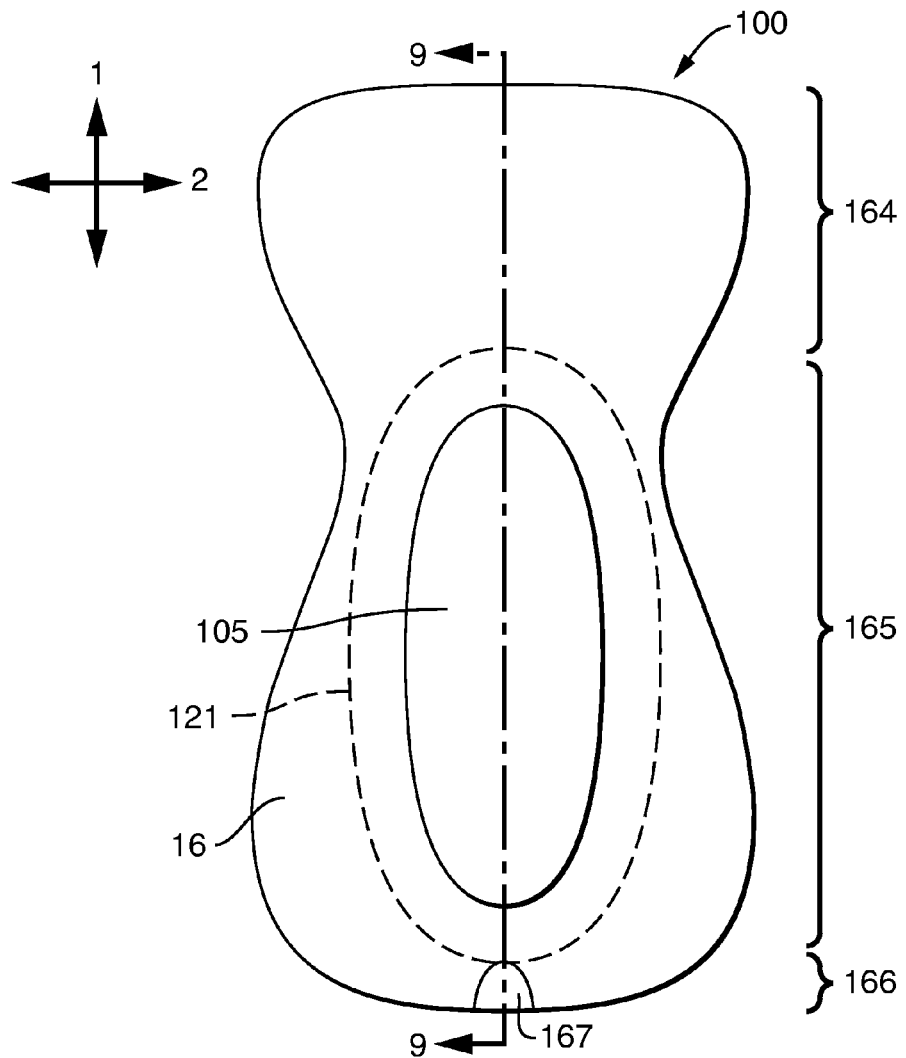
FIG. 9A shows a top view of another absorbent article of the present invention having a design for attachment to specific area of the body

To obtain an effective attachment to the body of the user, the shell 114 can be configured to be anatomically correct for a user. As is shown in FIG. 9A, the shape of the absorbent article 100 is such that it will correctly and securely fit in the vulva region of a user. The general shape of the absorbent article shown in FIG. 9A has been found to effectively attach to the vulva region of female users of the absorbent article.

Figure 9B:
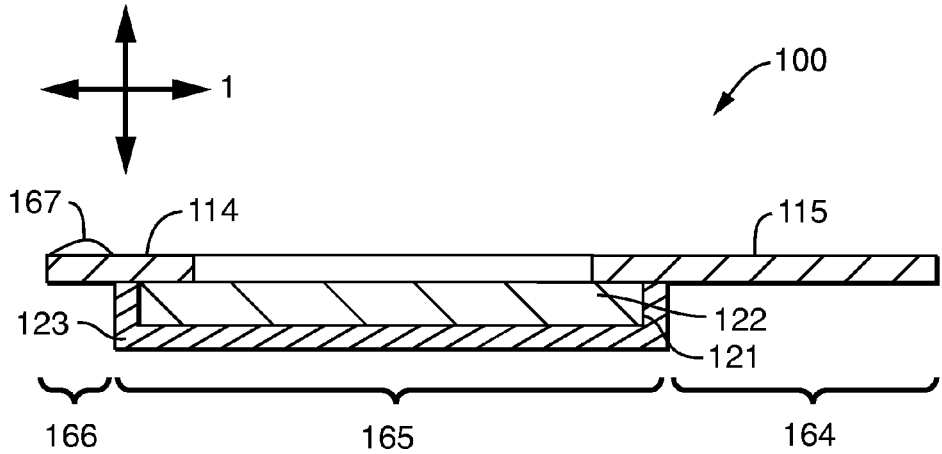
FIG. 9B shows a cross-section view of FIG. 9A along lines 9-9.

Additional features may be included to ensure an anatomically correct shape. For example, in the posterior region of the absorbent article 100, more particularly, the posterior region of the shell on the first side 115, the shell 114 may be imparted with a three-dimensional protrusion 167, as shown in FIGS. 9A and 9B. The protrusion 167 acts to fit comfortably in the perinea region of the user. The protrusion 167 may be formed from the shell material or may be formed from the body adhesive 144. By providing the three-dimensional protrusion 167, the absorbent article 100 can effectively fit to the typical body shape of the female user, thereby preventing leaks form the posterior portion of the absorbent article. The protrusion 167 may also serve as a guide to the user in placement of the absorbent article 100 on the body of a user prior to use.

Figure 10A:
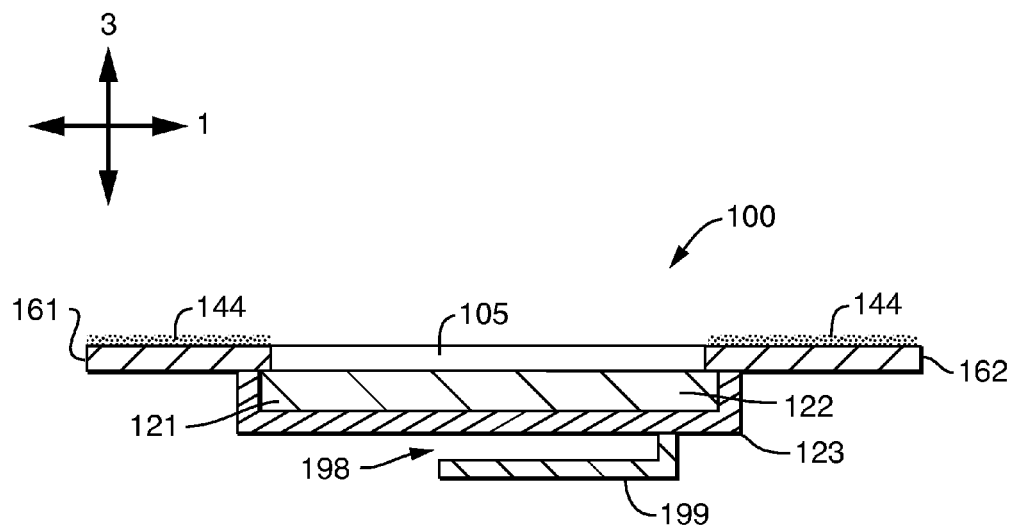
FIG. 10A and FIG. 10B shown embodiments of the present invention with placement guides.
Figure 10B:
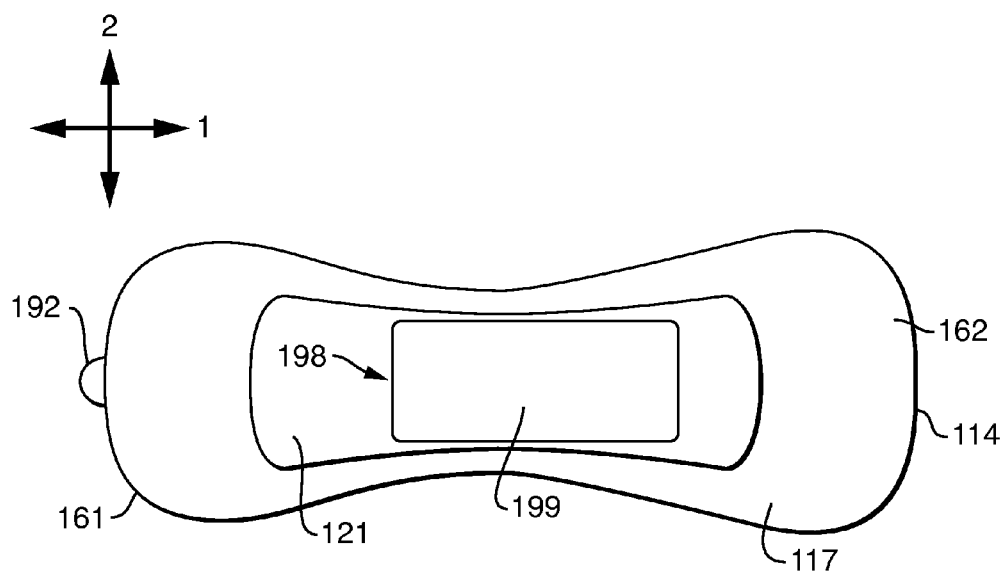

The absorbent article 100 of the present invention may have other features which aid the user to place and remove the absorbent article from the body. As is shown in FIGS. 10A and 10B, the second surface 117 of the shell 114 or the backsheet 123 may be provided with positioning aids such as a finger pocket 199, shown in FIG. 10A, or finger grooves in the shell 114 (not shown) material or backsheet 123 of the absorbent structure 121 as is shown in FIG. 10A. Generally, the finger pocket 199 has an opening 198 positioned such that a user inserts their fingers towards the posterior portion 166 or second end 162 of the absorbent article 100. The pocket 199 gives the user a location to place her fingers during placement of the absorbent article 100 onto the user's body. The pocket 199 may be an opening wide enough for the user to place at least two fingers in the pocket. Alternatively, there may be two or more openings which allow the user to place only one finger in each opening. Other similar positioning aids may be used to help guide a user to properly place the absorbent article for use. For example, grooves may be placed in the second surface 117 of the shell 114 or backsheet 123 of the absorbent structure. This may allow the user to feel the location of the absorbent structure relative to the vulva region during application of the absorbent article 10 to the vulva region of the body. The pocket 199 may also assist the user in removing the absorbent article from their body or removing the absorbent structure when it needs to be replaced.

The absorbent article 100 may also be provided with a removal aid which provides the user with an easy way to grasp and remove the absorbent article applied to the body. One particular removal aid is shown in FIG. 10B including a tab 192 located on the first end 161 of the shell which is not adhered to the body or is devoid of adhesive. Alternatively, other removal aids, such as having an area of the first end 161 being devoid of the body attaching adhesive 144 may be used. Other types of removal aid which may be present include loops and pull strings. The removal aid allows the user to effectively begin the process of gently removing the absorbent article from the body of the user, without the need of having to find a portion of the shell which may not be completely attached.

Other features or additives may be incorporated into the absorbent article of the present invention. For example, the absorbent article may contain an odor control agent, or a fragrance, skin wellness agents and other similar additives used in currently available absorbent articles. Any odor control agent or fragrance known to those skilled in the art may be used in the absorbent article 100 of the present invention. The odor control agent or fragrance may be added in various components of the absorbent article, including the shell 114, the absorbent structure 121, or the body adhesive 144. Skin wellness additives may be added onto the absorbent structure, any portion of the first surface 115 of the shell 114 attached to the user or in the body adhesive 144.

Generally, to apply the absorbent article 100 to the body of a user, the release sheet 146, protecting the absorbent structure and adhesive, if present, is removed from first surface of the shell. Next, the user positions the absorbent structure of the portion of the body in which absorbency is needed. If positioning pockets or other positioning aids are present on the absorbent structure, the user may optionally use these positioning aids to properly place the absorbent article for use. In the case of sanitary napkins and incontinence absorbent articles for females, the absorbent is positioned over the vagina area such that the absorbent structure will absorb body fluids. The user then checks to ensure that the first area 11 of the shell or the adhesive 144, if present, is contacting the skin around the vagina area.

If the absorbent article is intended to have a front and a back portion, the user first identifies the anterior portion 164 and/or the posterior portion 166 of the absorbent article. To aid in identification of the anterior and posterior portions, indicia located on the release sheet 146, shell 114 or absorbent material 121 viewable through the opening 105 in the shell 114 to indicate the anterior portion and/or posterior portion of the absorbent article may be present. Indicia can be simply lettering or a picture to indicate the front or back of the absorbent article. Once the anterior portion and posterior portion are identified by the user, the user places the absorbent article in the same manner described above. Examples of indicia which may be used include, color, wording, diagrams and the like, which would indicate to a user the anterior and posterior portions of the absorbent article.

In each case, the absorbent structure, which is designed to cover the labia majora of the user, may be positioned with the aid of the absorbent structure 121 or the opening 105. More specifically, the absorbent structure and/or the opening, when sized and shaped to the approximate size of the labia majora, can serve to guide the placement of the absorbent structure 121 over the labia majora. Once properly placed, pressure is applied by the user to the second surface 117 and or backing sheet 123 of the shell which will allow the first surface of the shell to contact the skin of the user, or to allow any adhesive applied to the first surface to be applied to the skin of the user.

By having the absorbent article 100 attached to the body of a user, the absorbent article 100 will tend to move with the skin of the user. This results in a comfortable to wear absorbent article which will be less likely to leak than conventional absorbent articles. The absorbent article has a very close-to-the-body fit which may provide improved discretion for the user.

Other benefits of the absorbent article 100 of the present invention may also be provided. For example, when the first side 115 of the shell has an adhesive applied thereto, upon removal of the absorbent article after use, the user may fold the first side of the shell onto itself to dispose of the used absorbent article. An effective seal may be formed around the perimeter of the shell, thereby effectively encapsulating the absorbent structure within a closure and the backing sheet of the absorbent layer. As a result, any odors associated with the absorbed fluids will be contained within the shell material and backing layer. Another use of the absorbent article of the present invention is a tampon backup absorbent article. The absorbent article could be effective in hiding the withdraw string of a tampon, while providing additional leakage protection.

The absorbent article described above can be an individual absorbent article or may be part of an absorbent system, offering the user a wide variety of options to fill the needs of the user. For example, the shell could be provided to users in a variety of shapes or sizes to allow users to select the appropriate shape or size for their given body shape. Likewise, the body adhesive may be provided in a variety of adhesive strengths to match the adhesive strength needed or desired by the user. By providing a variety of adhesive or other attachment means, a user could select the shells to match body type, body condition and other various factors that may vary from one user to another. Similarly, the absorbent structure could be provided in various absorbent capacities so that the user could select the appropriate absorbency to match the user's needs.

The absorbent system may be provided to users in a variety of packaging arrangements. In one packaging arrangement, a plurality of shells having different properties may be provided in separate packages or could be provided in a single package. It is generally a better packaging arrangement if shells having similar properties, shapes or sizes are provided in a single package. That is, in a given package, the user is provided with a plurality of shells all having the same shape, size, and properties, such as the body attachment properties. Regarding the absorbent structures, the absorbent structures could be provided to the user in packages sorted by absorbent capacity or various absorbent capacity structures could be provided in a single package. By having all absorbent structures in a single package with a single absorbent capacity, a user will able to select the correct absorbent capacity for their typical needs. However, by providing different absorbent capacity absorbent structures in a single package, the user will be provided with the ability to select the absorbent structure with the appropriate absorbent capacity for a given situation, without the need to purchase multiply package of absorbent structures.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An absorbent article for attachment to a wearer's skin in the vulva region of the wearer's torso, said article comprising:
   a shell comprising a first side and a second side, a first region having a pair of lateral side regions extending from the first region, said pair of lateral side regions each comprise a proximate end adjacent the first region and a distal end, and said pair of lateral side regions and the first region define an opening in the shell wherein the distal ends of each side region are not connected to one another through the shell and the opening is open near the distal ends of the side regions; and
   an absorbent structure attached to the second side of the shell such that at least a portion of the absorbent structure is positioned in the opening in the shell and a majority of the opening of the shell has the absorbent structure positioned therein;
   wherein when applied to the wearer the first side of the shell contacts to the wearer's skin surrounding vulva region and the shell is sized and shaped such that the first side of the shell only contacts the skin of the wearer proximate to the vulva region of the wearer.

2. The absorbent article according to claim 1, wherein the shell is prepared from a material comprising a woven web, a foam, nonwoven web, a gel, a film, a sheet of a polymeric material or a laminate of one or more of these materials.

3. The absorbent article according to claim 1, wherein at least a portion of the first side of the shell comprises an adhesive, wherein the adhesive attaches the absorbent article to the wearer's skin surrounding the vulva region of the wearer's body.

4. The absorbent article according to claim 3, wherein the first side of the shell is essentially entirely covered by the adhesive.

5. The absorbent article according to claim 1, wherein the first region forms an anterior portion and the second region forms a posterior portion of the absorbent article, the posterior portion is adapted to attach to the body of a user between the vulva region and the anal region of the body of the user and the anterior portion is adapted to attach to the mons Veneris region of a user.

6. The absorbent article according to claim 1, wherein the absorbent structure is attached to the second side of the shell with an adhesive, 7. The absorbent article according to claim 1, wherein the absorbent structure comprises an absorbent core and a liquid impermeable backsheet, wherein the absorbent core is positioned between the opening and the liquid impermeable backsheet or the second side of the shell and the liquid impermeable backsheet.

8. The absorbent article according to claim I. further comprising a release sheet attached to the first side of the shell.

9. The absorbent article according to claim 1, wherein the absorbent structure is removably attached to the second side of the shell.

10. The absorbent article according to claim 1, further comprising a placement aid.

11. The absorbent article according to claim 1, wherein the absorbent article comprises a sanitary napkin, a pantiliner or an incontinence absorbent article.

12. The absorbent article according to claim 1, wherein the absorbent structure is removable from the shell.

13. The absorbent article according to claim 1, wherein the opening comprises a permeable region which is permeable to body fluids.

14. An absorbent article for attachment to a wearer's skin in the vulva region of the wearer's torso, said article comprising:
  a shell comprising a first side and a second side, a first region having a pair of lateral side regions extending from the first region, said pair of lateral side regions each comprise a proximate end adjacent the first region and a distal end, and said pair of lateral side regions and the first region define an opening in the shell wherein the distal ends of each side region are not connected to one another through the shell and the opening, is open near the distal ends of the side regions; and
  an absorbent structure attached to the second side of the shell such that at least a portion of the absorbent structure is positioned in the opening in the shell and a majority of the opening of the shell has the absorbent structure positioned therein;
  wherein when applied to the wearer the first side of the shell contacts to the wearer's skin surrounding vulva region and the shell is sized and shaped such that the first side of the shell only contacts the skin of the wearer proximate to the vulva region of the wearer; and
  wherein the absorbent article comprises a longitudinal direction and a lateral direction, the shell being larger in both the longitudinal direction and the lateral direction than the absorbent structure.

15. The absorbent article according to claim 14, wherein the first side of the shell is essentially entirely covered by adhesive, wherein the adhesive provides a means to attach the absorbent article to the wearer's skin surrounding the vulva region of the wearer's body.

16. The absorbent article according to claim 14, further comprising a release sheet attached to the first side of the shell.

17. The absorbent article according to claim 14, further comprising a placement aid.

* * * * *